US010450546B2

(12) United States Patent
Goldman et al.

(10) Patent No.: US 10,450,546 B2
(45) Date of Patent: Oct. 22, 2019

(54) INDUCED PLURIPOTENT CELL-DERIVED OLIGODENDROCYTE PROGENITOR CELLS FOR THE TREATMENT OF MYELIN DISORDERS

(71) Applicant: UNIVERSITY OF ROCHESTER, Rochester, NY (US)

(72) Inventors: Steven A. Goldman, Webster, NY (US); Su Wang, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 14/764,507

(22) PCT Filed: Feb. 6, 2014

(86) PCT No.: PCT/US2014/015019
§ 371 (c)(1),
(2) Date: Jul. 29, 2015

(87) PCT Pub. No.: WO2014/124087
PCT Pub. Date: Aug. 14, 2014

(65) Prior Publication Data
US 2015/0352154 A1  Dec. 10, 2015

Related U.S. Application Data

(60) Provisional application No. 61/761,584, filed on Feb. 6, 2013, provisional application No. 61/780,265, filed on Mar. 13, 2013.

(51) Int. Cl.
C12N 5/071 (2010.01)
A01N 63/00 (2006.01)
C12N 5/079 (2010.01)
A61K 9/00 (2006.01)
A61K 35/30 (2015.01)

(52) U.S. Cl.
CPC .......... C12N 5/0622 (2013.01); A61K 9/0085 (2013.01); A61K 35/30 (2013.01); C12N 2506/02 (2013.01); C12N 2506/094 (2013.01); C12N 2506/45 (2013.01)

(58) Field of Classification Search
CPC ... C12N 5/0622; C12N 2506/45; A61K 35/30
USPC .......................................... 435/368; 424/93.7
See application file for complete search history.

(56) References Cited

U.S. PATENT DOCUMENTS

| 3,753,357 | A | 8/1973 | Schwartz |
| 4,199,022 | A | 4/1980 | Senkan et al. |
| 4,559,298 | A | 12/1985 | Fahy |
| 6,235,527 | B1 | 5/2001 | Rao et al. |
| 6,245,564 | B1 | 6/2001 | Goldman et al. |
| 6,361,996 | B1 | 3/2002 | Rao et al. |
| 6,497,872 | B1 | 12/2002 | Weiss et al. |
| 6,692,957 | B2 | 2/2004 | Goldman et al. |
| 6,734,015 | B1 | 5/2004 | Rao et al. |
| 6,787,353 | B1 | 9/2004 | Rao et al. |
| 6,830,927 | B2 | 12/2004 | Rao et al. |
| 6,852,532 | B2 | 2/2005 | Mayer-Proschel et al. |
| 6,900,054 | B2 | 5/2005 | Rao et al. |
| 7,037,720 | B2 | 5/2006 | Rao et al. |
| 7,150,989 | B2 | 12/2006 | Goldman et al. |
| 7,214,372 | B2 | 5/2007 | Rao et al. |
| 7,517,521 | B2 | 4/2009 | Mayer-Proschel et al. |
| 7,524,491 | B2 | 4/2009 | Goldman et al. |
| 7,595,194 | B2 | 9/2009 | Rao et al. |
| 7,795,021 | B2 | 9/2010 | Rao et al. |
| 8,168,174 | B2 | 5/2012 | Mayer-Proschel et al. |
| 8,206,669 | B2 | 6/2012 | Goldman et al. |
| 8,227,247 | B2 | 7/2012 | Zhang et al. |
| 3,263,402 | A1 | 9/2012 | Goldman et al. |
| 8,658,424 | B2 | 2/2014 | Zhang et al. |
| 8,673,292 | B2 | 3/2014 | Rao et al. |
| 8,709,807 | B2 | 4/2014 | Mayer-Proschel et al. |
| 9,371,513 | B2 | 6/2016 | Goldman et al. |
| 9,709,553 | B2 | 7/2017 | Goldman et al. |
| 2002/0012903 | A1 | 1/2002 | Goldman et al. |
| 2002/0061586 | A1 | 5/2002 | Goldman et al. |
| 2003/0049234 | A1 | 3/2003 | Goldman et al. |
| 2004/0253719 | A1 | 12/2004 | Goldman et al. |
| 2005/0084963 | A1 | 4/2005 | Chan-Ling |
| 2010/0159595 | A1 | 6/2010 | Zhang et al. |
| 2011/0059055 | A1 | 3/2011 | Goldman et al. |
| 2012/0100113 | A1 | 4/2012 | Tesar et al. |
| 2012/0177614 | A1 | 7/2012 | Kido |
| 2012/0207744 | A1 | 8/2012 | Mendlein et al. |
| 2012/0230963 | A1 | 9/2012 | Sandrock et al. |
| 2013/0004467 | A1 | 1/2013 | Goldman et al. |
| 2015/0328339 | A1 | 11/2015 | Goldman et al. |
| 2015/0352154 | A1 | 12/2015 | Goldman et al. |

(Continued)

FOREIGN PATENT DOCUMENTS

EP  2499238 B1  8/2014
EP  2379711 B1  11/2016

(Continued)

OTHER PUBLICATIONS

Allegrucci et al., 2006, Human Reproduction Update, vol. Advance Access published on Aug. 26, 2006, p. 1-18.*

(Continued)

Primary Examiner — Shin Lin Chen
(74) Attorney, Agent, or Firm — Pepper Hamilton LLP

(57) ABSTRACT

The present disclosure relates to a preparation of CD140a/PDGFRα positive cells that comprises oligodendrocyte progenitor cells co-expressing OLIG2 and CD140a/PDGFRα. The preparation of cells is derived from pluripotent cells that were derived from skin cells, fibroblasts, umbilical cord blood, peripheral blood, bone marrow, or other somatic cells. The cell preparation has an in vivo myelination efficiency that is equal to or greater than the in vivo myelination efficiency of a preparation of A2B5$^+$/PSA-NCAM$^-$sorted fetal human tissue derived oligodendrocyte progenitor cells. Methods of making, isolating and using the disclosed cell preparation are also described.

9 Claims, 12 Drawing Sheets
Specification includes a Sequence Listing.

(56) References Cited

U.S. PATENT DOCUMENTS

| | | |
|---|---|---|
| 2016/0264937 A1 | 9/2016 | Goldman et al. |
| 2017/0159015 A1 | 6/2017 | Goldman et al. |
| 2017/0182098 A1 | 6/2017 | Goldman |
| 2017/0198255 A1 | 7/2017 | Goldman et al. |
| 2017/0209494 A1 | 7/2017 | Goldman et al. |

FOREIGN PATENT DOCUMENTS

| | | |
|---|---|---|
| JP | 2011-155978 A | 8/2011 |
| WO | 94/10292 A1 | 5/1994 |
| WO | 98/32879 A1 | 7/1998 |
| WO | 99/49014 A1 | 9/1999 |
| WO | 01/46384 A2 | 6/2001 |
| WO | 01/178753 A2 | 10/2001 |
| WO | 03/070171 A2 | 8/2003 |
| WO | 2004/007696 A2 | 1/2004 |
| WO | 2012/095730 A1 | 7/2012 |

OTHER PUBLICATIONS

Rao, M., 2004, Developmental Biology, vol. 275, p. 269-286.*
Abeyta et al., 2004, Human Molecular Genetics, vol. 13, No. 6, p. 601-608.*
Narsinh et al., 2011, Molecular therapy, vol. 9, No. 4, p. 635-638.*
Bellin et al., 2012, Nature reviews/Molecular Cell Biology, vol. 13, p. 713-726.*
Burridge et al., 2011, PLoS ONE, vol. 6, No. 4, e18293, p. 1-16.*
Goldman et al., 2011, US 20110059055 A1.*
Totonchi et al., 2010, Int. J. Dev. Biol., vol. 54, p. 877-886.*
Abbaszadeh et al., "Bone Marrow Stromal Cell Transdifferentiation into Oligodendrocyte-Like Cells Using Triiodothyronine as a Inducer with Expression of Platelet-Derived Growth Factor Alpha as a Maturity Marker," Iranian Biomedical Journal 17(2):62-70 (2013).
Han et al., "Direct Reprogramming of Fibroblasts into Neural Stem Cells by Defined Factors," Cell Stem Cell 10:465-472 (2012).
Chua et al., "Neural Progenitors, Neurons and Oligodendrocytes from Human Umbilical Cord Blood Cells in a Serum-Free, Feeder-Free Cell Culture," Biochemical and Biophysical Research Communications 379:217-221 (2009).
Ben-Hur et al., "Prospects of Cell Therapy for Disorders of Myelin," Ann. N.Y. Acad. Sci. 1142:218-249 (2008).
Windrem et al., "Neonatal Chimerization with Human Glial Progenitor Cells Can Both Remyelinate and Rescue the Otherwise Lethally Hypomyelinated Shiverer Mouse," Cell Stem Cell 2:553-565 (2008).
Supplementary Search Report and Search Opinion for EP14749594.9 dated Jun. 20, 2016.
Goldman et al., "Glial Progenitor Cell-Based Treatment and Modeling of Neurological Disease," Science 338:491-495 (2012).
Sim et al., "CD140a Identifies a Population of Highly Myelinogenic, Migration-Competent and Efficiently Engrafting Human Oligodendrocyte Progenitor Cells," Nature Biotechnology 29(10):934-942 (2011).
Pouya et al., "Human Induced Pluripotent Stem Cells Differentiation into Oligodendrocyte Progenitors and Transplantation in a Rat Model of Optic Chiasm Demyelination," PLos One 6(11):e27925 (2011).
Wang et al., "Human iPSC-Derived Oligodendrocyte Progenitor Cells Can Myelinate and Rescue a Mouse Model of Congenital Hypomyelination," Cell Stem Cell 12:252-264 (2013).
International Search Report and Written Opinion for corresponding application No. PCT/US14/15019 dated May 7, 2014.
International Preliminary Report on Patentability for International Application No. PCT/US14/15019 (dated Aug. 11, 2015).
Sim et al., "Fate Determination of Adult Human Glial Progenitor Cells," Neuron Glia Biol. 5(3/4): 45-55 (2009).
UniProt, UniProtKB—P16234 (PDGFRA_Human), available at http://www.uniprot.org/uniprot/P16234, accessed Jan. 20, 2016.

Office Action for Canadian Patent Application No. 2,723,382, 6 pages (dated May 27, 2015).
Written Opinion for International Application No. PCT/US2009/043140, 6 pages (dated Mar. 8, 2010).
International Preliminary Report on Patentability for International Application No. PCT/US2009/043140 (dated Nov. 9, 2010).
International Search Report for International Application No. PCT/US2009/043140 (dated Mar. 8, 2010).
Summons to Attend Oral Proceedings for corresponding European Patent Application No. 09743660.4, 5 pages (dated Sep. 28, 2015).
European Search Report for European Patent Application No. 09743660.4 (dated Dec. 12, 2011).
Communication for European Patent Application No. 09743660.4 (dated Mar. 21, 2014).
Chung et al., "Human Embryonic Stem Cell Lines Generated without Embryo Destruction," Cell Stem Cell 2(2):113-117 (2008).
Li et al., "Oligodendrocyte Progenitor Cells in the Adult Rat CNS Express Myelin Oligodendrocyte Glycoprotein (MOG)," Brain Pathol. 12(4):463-471 (2002).
Crang et al., "The Demonstration by Transplantation of the Very Restricted Remyelinating Potential of Post-Mitotic Oligodendrocytes," J. Neurocytol.27(7):541-553 (1998).
http://www.pierce-antibodies.com/PDGF-RA--CD140a-antibody-Polyclonal--PA532545.html.
Scolding et al., "Oligodendrocyte Progenitors are Present in the Normal Adult Human CNS and in the Lesions of Multiple Sclerosis," Brain 121:2221-8 (1998).
PE anti-human CD140a (PDGFRalpha) antibody http://www/biolegend.com/pe-anti-human-cd140a-pdgfralpha-antibody-3727.html.
Berry et al., "Cytology and Lineage of NG2-Positive Glia," Journal of Neurocytology 31:457-467 (2002).
Terada et al., "The Tetraspanin Protein, CD9, Is Expressed by Progenitor Cells Committed to Oligodendrogenesis and Is Linked to β1 Integrin, CD81, and Tspan-2," GLIA 40:350-359 (2002).
Armstrong et al., "Pre-Oligodendrocytes from Adult Human CNS," J. Neurosci. 12(4):1538-47 (1992).
Dennis et al., "DAVID: Database for Annotation, Visualization, and Integrated Discovery," Genome Biol. 4:R60 (2003).
Gentleman et al., "Bioconductor: Open Software Development for Computational Biology and Bioinformatics," Genome Biol. 5(10):R80-R80.16 (2004).
Hall et al., "Spinal Cord Oligodendrocytes Develop from Ventrally Derived Progenitor Cells that Express PDGF alpha-Receptors," Development 122:4085-94 (1996).
Irizarry et al., "Exploration, Normalization, and Summaries of High Density Oligonucleotide Array Probe Level Data," Biostatistics 4(2):249-64 (2003).
Keyoung et al., "High-Yield Selection and Extraction of Two Promoter-Defined Phenotypes of Neural Stem Cells from the Fetal Human Brain," Nature Biotechnology 19:843-50 (2001).
Kirschenbaum et al., "In vitro Neuronal Production and Differentiation by Precursor Cells Derived from the Adult Human Forebrain," Cerebral Cortex 4(6):576-89.
LaRochelle et al., "Inhibition of Platelet-Derived Growth Factor Autocrine Growth Stimulation by a Monoclonal Antibody to the Human alpha Platelet-Derived Growth Factor Receptor," Cell Growth Differ. 4(7):547-53 (1993).
Limner et al., "A New Technique for Removal of Amorphous Phase Tissue Water Without Ice Crystal Damage: A Preparative Method for Ultrastructural Analysis and Immunoelectron Microscopy," J. Histochem. Cytochem. 34(9):1123-35 (1986).
Matsui et al., "Independent Expression of Human α or β Platelet-Derived Growth Factor Receptor cDNAs in a Näive Hematopoietic Cell Leads to Functional Coupling with Mitogenic and Chemotactic Signaling Pathways," Proc. Natl. Acad. Sci. USA 86:8314-18 (1989).
Mazur, "The Role of Intracellular Freezing in the Death of Cells Cooled at Supraoptinial Rates," Cryobiology 14:251-72 (1977).
Munson et al. "Ligand: A Versatile Computerized Approach for Characterization of Ligand-Binding Systems," Anal. Biochem. 107:220-39 (1980).

(56) References Cited

OTHER PUBLICATIONS

Nunes et al., "Identification and Isolation of Multipotent Neural Progenitor Cells from the Subcortical White Matter of the Adult Human Brain," Nature Medicine 9(4):439-47 (2003).
Pringle et al., "PDGF Receptors in the Rat CNS: During Late Neurogenesis, PDGF Alpha-Receptor Expression Appears to be Restricted to Glial Cells of the Oligodendrocyte Lineage," Development 115:535-51 (1992).
Rasband et al., "Developmental Clustering of ion Channels at and Near the Node of Ranvier," Dev. Biol., 236(1):5-16 (2001).
Readhead et al., "Expression of a Myelin Basic Protein Gene in Transgenic Shiverer Mice: Correction of the Dysmyelinating Phenotype," Cell 48:703-12 (1990).
Roy et al., "Identification, Isolation, and Promoter-Defined Separation of Mitotic Oligodendrocyte Progenitor Cells from the Adult Human Subcortical White Matter," J. Neurosci., 19(22) 9986-95 (1999).
Roy et al., "In vitro Neurogenesis by Progenitor Cells Isolated from the Adult Human Hippocampus," Nature Med. 6:271-7 (2000).
Roy et al.. "Telomerase-Immortalization of Neuronally Restricted Progenitor Cells Derived from the Human Fetal Spinal Cord," Nature Biotechnol., 22:297-305 (2004).
Schafer et al., "Glial Regulation of the Axonal Membrane at Nodes of Ranvier," Curr. Opinion in Neurobiology 16:508-14 (2006).
Sherman et al., "Mechanisms of Axon Ensheathment and Myelin Growth," Nature Rev. Neurosci. 6:683-90 (2005).
Shinkai et al., "RAG-2 Deficient Mice Lack Mature Lymphocytes Owing to Inability to Initiate V(D)J Rearrangement," Cell 68(5): 855-67 (1992).
Sim et al., "Complementary Patterns of Gene Expression by Human Oligodendrocyte Progenitors and their Environment Predict Determinants of Progenitor Maintenance and Differentiation," Ann. Neurol. 59(5):763-79 (2006).
Smyth, "Linear Models and Empirical Bayes Methods for Assessing Differential Expression in Microarray Experiments," Stal. Appl. Genel. Mol. Bio. 3:Article 3 (2004).
Takahashi et al., "Induction of Pluripotent Stem Cells from Mouse Embryonic and Adult Fibroblast Cultures by Defined Factors," Cell 126(4):663-76 (2006).
Windrem et al., "Progenitor Cells Derived from the Adult Human Subcortical White Matter Disperse and Differentiate as Oligodendrocytes within Demyelinated Lesions of the Rat Brain," J. Neurosci. Res. 69(6):966-75 (2002).
Windrem et al., "Fetal and Adult Human Oligodendrocyte Progenitor Cell Isolates Myelinate the Congenitally Dysmyelinated Brain," Nature Medicine 10(1):93-7 (2004).
Yang et al., "βIV Spectrin is Recruited to Axon Initial Segments and Nodes of Ranvier by Ankyrin G," J. Cell Biol. 176:509-19 (2007).
Yu et al., "Induced Pluripotent Stem Cell Lines Derived from Human Somatic Cells," Science 318(5858):1917-20 (2007).
Office Action in U.S. Appl. No. 12/990,874 (dated Nov. 10, 2016).
Office Action in U.S. Appl. No. 12/990,874 (dated May 4, 2016).
Office Action in U.S. Appl. No. 12/990,874 (dated Oct. 20, 2015).
Office Action in U.S. Appl. No. 12/990,874 (dated May 14, 2014).
Office Action in U.S. Appl. No. 12/990,874 (dated Mar. 15, 2013).
Hu et al., "Neural Differentiation of Human Induced Pluripotent Stem Cells Follows Developmental Principles But With Variable Potency," Proc Natl Acad Sci USA 107(9):4335-40 (2010).
Hu et al., "Differentiation of Human Oligodendrocytes From Pluripotent Stem Cells," Nat Protoc. 4(11):1614-22 (2009).
Hu et al., "Human Oligodendrocytes From Embryonic Stem Cells: Conserved SHH Signaling Networks and Divergent FGF Effects," Development 136(9):1443-52 (2009).
Sullivan et al., "Induced Pluripotent Stem Cells: Epigenetic Memories and Practical Implications," Mol Hum Reprod 16(12):880-5 (2010).
Chin et al., "Induced Pluripotent Stem Cells and Embryonic Stem Cells are Distinguished by Gene Expression Signatures," Cell Stem Cell 5(1):111-23 (2009).

Vaskova et al., ""Epigenetic Memory" Phenomenon in Induced Pluripotent Stem Cells," Acta Naturae. Oct. 2013;5(4):15-21.
Notice of Reasons for Rejections for JP 2015-557053 dated Dec. 4, 2017.
Alsanie et al., "Human Embryonic Stem Cell-Derived Oligodendrocytes: Protocols and Perspectives," Stem Cells and Developments 22(18):2459-2476 (2013).
Hatch et al., "Derivation of High-Purity Oligodendroglial Progenitors," Methods in Molecular Biology 549:59-74 (2009).
Akiyama et al., "Transplantation of Clonal Neural Precursor Cells Derived from Adult Human Brain Establishes Functional Peripheral Myelin in the Rat Spinal Cord," Exp. Neuro. 167:27-39 (2001).
Alenzi et al., "Stem Cells: Biology and Clinical Potential," African Journal of Biotechnology 10(86): 19929-19940 (2011).
Auvergne et al., "Transcriptional Differences Between Normal and Glioma-Derived Glial Progenitor Cells Identify a Core Set of Dysregulated Genes," Cell Reports 3:2127-2141 (2013).
Benraiss et al., "Sustained Mobilization of Endogenous Neural Progenitors Delays Disease Progression in a Transgenic Model of Huntington's Disease," Cell Stem Cell 12:787-799 (2013).
Blakemore et al., "Extensive Oligodendrocyte Remyelination Following Injection of Cultured Central Nervous System Cells into Demyelinating Lesions in Adult Central Nervous System," Dev. Neurosci. 10:1-11 (1988).
Cao et al., "Stern Cell Repair of Central Nervous System Injury," Journal of Neuroscience Research 68:501-510 (2002).
Database Accession No. PREV200100486585 (2001).
Emerich et al., "Recent Efforts to Overcome the Blood-Brain Barrier for Drug Delivery," Exp. Opin. Ther. Patents 10(3):279-287 (2000).
Espinosa De Los Monteros et al., "Remyelination of the Adult Demyelinated Mouse Brain by Grafted Oligodendrocyte Progenitors and the Effect of B-104 Cografts," Neurochemical Res. 26(6):673-682 (2001).
Franklin, "Why Does Remyelination Fail in Multiple Sclerosis?" Nature Rev. Neurosci. 3(9):705-714 (2002).
Gallo et al., "Oligodendrocyte Progenitor Cell Proliferation and Lineage Progression are Regulated by Glutamate Receptor-Mediated K+ Channel Block," J. Neurosci. 16(8): 2659-2670 (1996).
Gensert et al., "Endogenous Progenitors Remyelinate Demyelinated Axons in the Adult CNS," Neuron 19:197-203 (1997).
Godfraind et al., "In Vivo Analysis of Glial Cells Phenotypes During a Viral Demyelinating Disease in Mice," J. Cell Biol. 109:2405-2416 (1989).
Goldman and Windrem, "Stem Cell-Based Strategies for Treating Pediatric Disorders of Myelin," Human Molecular Genetics 17(10): R76-R83 (2008).
Goldman et al., "How to Make an Oligodendrocyte," Development 142:3983-3995 (2015).
Gout et al., "Remyelination by Transplanted Oligodendrocytes of a Demyelinated Lesion in the Spinal Cord of the Adult Shiverer Mouse," Neurosci. Lett. 87:195-199 (1988).
Gumpel et al., "Myelination and Remyelination in the Central Nervous System by Transplanted Oligodendrocytes Using the Shiverer Model," Dev. Neurosci. 11:132-139 (1989).
Izrael et al., "Human Oligodendrocytes Derived From Embryonic Stem Cells: Effect of Noggin on Phenotypic Differentiation In Vitro and on Myelination In Vivo," Mol Cell Neurosci. 34(3):310-23 (2007).
Jeffery et al., "Behavioural Consequences of Oligodendrocyte Progenitor Cell Transplantation into Experimental Demyelinating Lesions in the Rat Spinal Cord," Eur. J. Neurosci. 11:1508-1514 (1999).
K.A. Nave, "Neurological Mouse Mutants and the Genes of Myelin," J. Neurosci. Res. 38(6):607-12 (1994).
Keirstead et al., "Human Embryonic Stem Cell-Derived Oligodendrocyte Progenitor Cell Transplants Remyelinate and Restore Locomotion After Spinal Cord Injury," J Neurosci. 25(19):4694-705 (2005).
Kennea et al., "Neural Stem Cells," Journal of Pathology 197:536-550 (2002).
Kolf et al., "Biology of Adult Mesenchymal Stem Cells: Regulation of Niche, Self-Renewal and Differentiation," Arthritis Research & Therapy 9(204):204-213 (2007).

(56) References Cited

OTHER PUBLICATIONS

Lachapelle et al., "Transplantation of CNS Fragments into the Brain of Shiverer Mutant Mice: Extensive Myelination by Implanted Oligodendrocytes," Dev. Neurosci. 6:325-334 (1983).
Learish et al., "Intraventricular Transplantation of Oligodendrocyte Progenitors into a Fetal Myelin Mutant Results in Widespread Formation of Myelin," Annals of Neurology 46(5):716-722 (1999).
Mehler et al., "Progenitor Cell Biology: Implications for Neural Regeneration," Archives of Neurology 56(7):780-784 (1999).
Milward et al., "Isolation and Transplantation of Multipotential Populations of Epidermal Growth Factor-Responsive, Neural Progenitor Cells from the Canine Brain," Journal of Neuroscience Research 50:862-871 (1997).
Office Action for U.S. Appl. No. 15/427,986 (dated Apr. 18, 2018).
Rossi et al., "Neural Stem Cell Therapy for Neurological Diseases: Dreams and Reality," Nature Reviews Neuroscience 3:401-409 (2002).
Scolding et al., "Identification of A2B5-Positive Putative Oligodendrocyte Progenitor Cells and A2B5-Positive Astrocytes in Adult Human White Matter," Neurosci. 89(1):1-4 (1999).
Seilhean et al., "Myelination by Transplanted Human and Mouse Central Nervous System Tissue After Long-term Cryopreservation;" Acta Neuropathologica 91(1):82-88 (1996).
Talan J., "Human Glial Progenitor Cells Remyelinate in Shiverer Mouse: Plans to Study Cell Grafts in Children with Myelin Disease," Neurology Today 8(14):1 (2008).
Tyszka et al., "Statistical Diffusions Tensor Histology Reveals Regional Dysmyelination Effects in the Shiverer Mouse Mutant," NeuroImage 29(4):1058-65 (2006).
Wang et al., "Isolation of Neuronal Precursors by Sorting Embryonic Forebrain Transfected with GFP Regulated by the Ta1 Tubulin Promoter," Nature Biotechnology 16:196-201 (1998).
Yang et al., "A Novel Approach for Amplification and Purification of Mouse Oligodendrocyte Progenitor Cells," Frontiers in Cellular Neuroscience 10:article 203, p. 1-10 (2016).
Yandava et al., "'Global' Cell Replacement is Feasible via Neural Stem Cell Transplantation: Evidence from the Dysmyelinated Shiverer Mouse Brain," Proc. Natl. Acad. Sci. USA 96:7029-7034 (1999).
Warrington et al., "Differential Myelinogenic Capacity of Specific Developmental Stages of the Oligodendrocyte Lineage Upon Transplantation Into Hypomyelinating Hosts," J. Neurosci. Res.34:1-13 (1993).
Gumpel et al., "Transplantation of Human Embryonic Oligodendrocytes into Shiverer Brain," Ann. NY Acad. Sci. 495:71-85 (1987).
Lokker et al., "Functional Importance of Platelet-derived Growth Factor (PDGF) Receptor Extracellular Immunoglobulin-like Domains," J. Biol. Chem. 272(52):33037-44 (1997).
Search result of PDGFRA at The Human Protein Atlas (www.Proteinatlas.org).
Notice of Reasons for Rejections for JP 2015-557053 dated Nov. 12, 2018.

* cited by examiner

SEQUENCE LISTING

```
<160> NUMBER OF SEQ ID NOS: 26

<210> SEQ ID NO 1
<211> LENGTH: 21
<212> TYPE: DNA
<213> ORGANISM: Artificial
<220> FEATURE:
<223> OTHER INFORMATION: Primer

<400> SEQUENCE: 1
cgtctccaca catcagcaca a                                              21

<210> SEQ ID NO 2
<211> LENGTH: 22
<212> TYPE: DNA
<213> ORGANISM: Artificial
```

```
<220> FEATURE:
<223> OTHER INFORMATION: Primer

<400> SEQUENCE: 2
tcttggcagc aggatagtcc tt                                          22

<210> SEQ ID NO 3
<211> LENGTH: 18
<212> TYPE: DNA
<213> ORGANISM: Artificial
<220> FEATURE:
<223> OTHER INFORMATION: Primer

<400> SEQUENCE: 3
ccacccatgg caaattcc                                               18

<210> SEQ ID NO 4
<211> LENGTH: 22
<212> TYPE: DNA
<213> ORGANISM: Artificial
<220> FEATURE:
<223> OTHER INFORMATION: Primer

<400> SEQUENCE: 4
tgggatttcc attgatgaca ag                                          22

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
catcgagatc gccacctaca                                             20

<210> SEQ ID NO 6
<211> LENGTH: 19
<212> TYPE: DNA
<213> ORGANISM: Artificial
<220> FEATURE:
<223> OTHER INFORMATION: Primer

<400> SEQUENCE: 6
tctgcacggg aatggtgat                                              19

<210> SEQ ID NO 7
<211> LENGTH: 17
<212> TYPE: DNA
<213> ORGANISM: Artificial
<220> FEATURE:
<223> OTHER INFORMATION: Primer

<400> SEQUENCE: 7
tgcggccgat tgtgaac                                                17

<210> SEQ ID NO 8
<211> LENGTH: 21
<212> TYPE: DNA
<213> ORGANISM: Artificial
<220> FEATURE:
<223> OTHER INFORMATION: Primer

<400> SEQUENCE: 8
cctcttttct ctgcggaacg t                                           21
```

-continued

```
<210> SEQ ID NO 9
<211> LENGTH: 22
<212> TYPE: DNA
<213> ORGANISM: Artificial
<220> FEATURE:
<223> OTHER INFORMATION: Primer

<400> SEQUENCE: 9
accaggcact accgtaaaca ca                                              22

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
ggtccgacct ggaaaatgct                                                 20

<210> SEQ ID NO 11
<211> LENGTH: 21
<212> TYPE: DNA
<213> ORGANISM: Artificial
<220> FEATURE:
<223> OTHER INFORMATION: Primer

<400> SEQUENCE: 11
ccaaaggcaa acaacccact t                                               21

<210> SEQ ID NO 12
<211> LENGTH: 20
<212> TYPE: DNA
<213> ORGANISM: Artificial
<220> FEATURE:
<223> OTHER INFORMATION: Primer

<400> SEQUENCE: 12
tcttgaccgg gaccttgtct                                                 20

<210> SEQ ID NO 13
<211> LENGTH: 17
<212> TYPE: DNA
<213> ORGANISM: Artificial
<220> FEATURE:
<223> OTHER INFORMATION: Primer

<400> SEQUENCE: 13
ggcgggcatt ccctttt                                                    17

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
cgagctgtac tgggcgttgt                                                 20

<210> SEQ ID NO 15
<211> LENGTH: 22
<212> TYPE: DNA
<213> ORGANISM: Artificial
<220> FEATURE:
<223> OTHER INFORMATION: Primer
```

<400> SEQUENCE: 15
tggtccgagt gtggttctgt aa                                              22

<210> SEQ ID NO 16
<211> LENGTH: 21
<212> TYPE: DNA
<213> ORGANISM: Artificial
<220> FEATURE:
<223> OTHER INFORMATION: Primer

<400> SEQUENCE: 16
tgtgcatagt cgctgcttga t                                               21

<210> SEQ ID NO 17
<211> LENGTH: 18
<212> TYPE: DNA
<213> ORGANISM: Artificial
<220> FEATURE:
<223> OTHER INFORMATION: Primer

<400> SEQUENCE: 17
ggcgcgcaac tacatcct                                                   18

<210> SEQ ID NO 18
<211> LENGTH: 19
<212> TYPE: DNA
<213> ORGANISM: Artificial
<220> FEATURE:
<223> OTHER INFORMATION: Primer

<400> SEQUENCE: 18
cgctcaccag tcgcttcat                                                  19

<210> SEQ ID NO 19
<211> LENGTH: 19
<212> TYPE: DNA
<213> ORGANISM: Artificial
<220> FEATURE:
<223> OTHER INFORMATION: Primer

<400> SEQUENCE: 19
tcgggcacca cttcaacag                                                  19

<210> SEQ ID NO 20
<211> LENGTH: 20
<212> TYPE: DNA
<213> ORGANISM: Artificial
<220> FEATURE:
<223> OTHER INFORMATION: Primer

<400> SEQUENCE: 20
tccgggaact tgaactggaa                                                 20

<210> SEQ ID NO 21
<211> LENGTH: 19
<212> TYPE: DNA
<213> ORGANISM: Artificial
<220> FEATURE:
<223> OTHER INFORMATION: Primer

<400> SEQUENCE: 21
ccttggtggc accccttac                                                  19

```
<210> SEQ ID NO 22
<211> LENGTH: 22
<212> TYPE: DNA
<213> ORGANISM: Artificial
<220> FEATURE:
<223> OTHER INFORMATION: Primer

<400> SEQUENCE: 22
tccggtaccc actcttgatc tt                                              22

<210> SEQ ID NO 23
<211> LENGTH: 16
<212> TYPE: DNA
<213> ORGANISM: Artificial
<220> FEATURE:
<223> OTHER INFORMATION: Primer

<400> SEQUENCE: 23
tgcgagcgct gcacat                                                     16

<210> SEQ ID NO 24
<211> LENGTH: 24
<212> TYPE: DNA
<213> ORGANISM: Artificial
<220> FEATURE:
<223> OTHER INFORMATION: Primer

<400> SEQUENCE: 24
gcagcgtgta cttatccttc ttca                                            24

<210> SEQ ID NO 25
<211> LENGTH: 22
<212> TYPE: DNA
<213> ORGANISM: Artificial
<220> FEATURE:
<223> OTHER INFORMATION: Primer

<400> SEQUENCE: 25
ccacgaggta atgtccaaca tg                                              22

<210> SEQ ID NO 26
<211> LENGTH: 18
<212> TYPE: DNA
<213> ORGANISM: Artificial
<220> FEATURE:
<223> OTHER INFORMATION: Primer

<400> SEQUENCE: 26
cattgggcgg caggtact                                                   18
```

INDUCED PLURIPOTENT CELL-DERIVED OLIGODENDROCYTE PROGENITOR CELLS FOR THE TREATMENT OF MYELIN DISORDERS

This application claims the benefit of U.S. Provisional Patent Application Ser. Nos. 61/761,584, filed Feb. 6, 2013, and 61/780,265, filed Mar. 13, 2013, which are hereby incorporated by reference in their entirety.

FIELD OF THE INVENTION

The present invention relates to preparations of induced pluripotent cell-derived oligodendrocyte progenitor cells, and methods of making, isolating, and using these cells.

BACKGROUND OF THE INVENTION

A broad range of diseases, from the inherited leukodystrophies to vascular leukoencephalopathies to multiple sclerosis, result from myelin injury or loss. In the pediatric leukodystrophies, in particular, compact myelin either fails to properly develop, or is injured in the setting of toxic storage abnormalities. Recent studies have focused on the use of transplanted oligodendrocytes or their progenitors for the treatment of these congenital myelin diseases. Both rodent and human-derived cell implants have been assessed in a variety of experimental models of congenital dysmyelination. The myelinogenic potential of implanted brain cells was first noted in the shiverer mouse (Lachapelle et al., "Transplantation of CNS Fragments Into the Brain of Shiverer Mutant Mice: Extensive Myelination by Implanted Oligodendrocytes," *Dev. Neurosci* 6:325-334 (1983)). The shiverer is a mutant deficient in myelin basic protein (MBP), by virtue of a premature stop codon in the MBP gene that results in the omission of its last 5 exons (Roach et al., "Chromosomal Mapping of Mouse Myelin Basic Protein Gene and Structure and Transcription of the Partially Deleted Gene in Shiverer Mutant Mice," *Cell* 42:149-155 (1985)). Shiverer is an autosomal recessive mutation, and shi/shi homozygotes fail to develop central compact myelin. They die young, typically by 20-22 weeks of age, with ataxia, dyscoordination, spasticity, and seizures. When fetal human brain tissue was implanted into shiverers, evidence of both oligodendrocytic differentiation and local myelination was noted (Lachapelle et al., "Transplantation of Fragments of CNS Into the Brains of Shiverer Mutant Mice: Extensive Myelination by Implanted Oligodendrocytes," *Dev. Neurosci* 6:326-334 (1983); Gumpel et al., "Transplantation of Human Embryonic Oligodendrocytes Into Shiverer Brain," *Ann NY Acad Sci* 495:71-85 (1987); and Seilhean et al., "Myelination by Transplanted Human and Mouse Central Nervous System Tissue After Long-Term Cryopreservation," *Acta Neuropathol* 91:82-88 (1996)). However, these unfractionated implants yielded only patchy remyelination and would have permitted the co-generation of other, potentially undesired phenotypes. Enriched glial progenitor cells were thus assessed for their myelinogenic capacity, and were found able to myelinate shiverer axons (Warrington et al., "Differential Myelinogenic Capacity of Specific Development Stages of the Oligodendrocyte Lineage Upon Transplantation Into Hypomyelinating Hosts," *J. Neurosci Res* 34:1-13 (1993)), though with low efficiency, likely due to predominantly astrocytic differentiation by the grafted cells. Yandava et al., "Global Cell Replacement is Feasible via Neural Stem Cell Transplantation: Evidence from the Dysmyelinated Shiverer Mouse Brain," *Proc. Natl. Acad. Sci.* 96:7029-7034 (1999), subsequently noted that immortalized multipotential progenitors could also contribute to myelination in shiverers. Duncan and colleagues similarly noted that oligosphere-derived cells raised from the neonatal rodent subventricular zone could engraft another dysmyelinated mutant, the myelin-deficient rat, upon perinatal intraventricular administration (Learish et al., "Intraventricular Transplantation of Oligodendrocyte Progenitors into a Fetal Myelin Mutant Results in Widespread Formation of Myelin," *Ann Neurol* 46:716-722 (1999)).

Human glial progenitor cells capable of oligodendrocytic maturation and myelination have been derived from both fetal and adult human brain tissue (Dietrich et al., "Characterization of A2B5+ Glial Precursor Cells From Cryopreserved Human Fetal Brain Progenitor Cells," *Glia* 40:65-77 (2002), Roy et al., "Identification, Isolation, and Promoter-Defined Separation of Mitotic Oligodendrocyte Progenitor Cells From the Adult Human Subcortical White Matter," *J. Neurosci.* 19:9986-9995 (1999), Windrem et al., "Fetal and Adult Human Oligodendrocyte Progenitor Cell Isolates Myelinate the Congenitally Dysmyelinated Brain," *Nat. Med.* 10:93-97 (2004)), as well as from human embryonic stem cells (Hu et al., "Differentiation of Human Oligodendrocytes From Pluripotent Stem Cells," *Nat. Protoc.* 4:1614-1622 (2009), Izrael et al., "Human Oligodendrocytes Derived From Embryonic Stem Cells: Effect of Noggin on Phenotypic Differentiation in Vitro and on Myelination in Vivo," *Mol. Cell. Neurosci.* 34:310-323 (2007), and Keirstead et al., "Human Embryonic Stem Cell-Derived Oligodendrocyte Progenitor Cell Transplants Remyelinate and Restore Locomotion After Spinal Cord Injury," *J. Neurosci.* 25:4694-4705 (2005)) and have proven effective in experimental models of both congenitally dysmyelinated (Sim et al., "CD140a Identifies a Population of Highly Myelinogenic, Migration-Competent and Efficiently Engrafting Human Oligodendrocyte Progenitor Cells," *Nat. Biotechnol.* 29:934-941 (2011), Windrem et al., "Fetal and Adult Human Oligodendrocyte Progenitor Cell Isolates Myelinate the Congenitally Dysmyelinated Brain," *Nat. Med.* 10:93-97 (2004), Windrem et al., "Neonatal Chimerization With Human Glial Progenitor Cells Can Both Remyelinate and Rescue the Otherwise Lethally Hypomyelinated Shiverer Mouse," *Cell Stem Cell* 2:553-565 (2008)) and adult demyelinated (Windrem et al., "Progenitor Cells Derived From the Adult Human Subcortical White Matter Disperse and Differentiate as Oligodendrocytes Within Demyelinated Lesions of the Rat Brain," *J. Neurosci. Res.* 69:966-975 (2002)) brain and spinal cord. Yet these successes in immunodeficient mice notwithstanding, immune rejection has thus far hindered the use of allogeneic human cells as transplant vectors. Concern for donor cell rejection has been especially problematic in regards to the adult demyelinating diseases such as multiple sclerosis, in which the inflammatory processes underlying these disorders can present an intrinsically hostile environment to any allogeneic grafts (Keyoung and Goldman, "Glial Progenitor-Based Repair of Demyelinating Neurological Diseases," *Neurosurg. Clin. N. Am.* 18:93-104 (2007)).

The present invention is directed at overcoming this and other deficiencies in the art.

SUMMARY OF THE INVENTION

A first aspect of the present invention is directed to a preparation of CD140a/PDGFRα positive cells where the preparation comprises oligodendrocyte progenitor cells coexpressing OLIG2 and CD140a/PDGFRα, and where the preparation of cells is derived from pluripotential cells derived from skin cells.

A second aspect of the present invention is directed to a preparation of CD140a/PDGFRα positive cells where the preparation comprises oligodendrocyte progenitor cells co-expressing OLIG2 and CD140a/PDGFRα, and where the preparation of cells is derived from pluripotential cells derived from umbilical cord blood.

Another aspect of the present invention is directed to a preparation of CD140a/PDGFRα positive cells where the preparation comprises oligodendrocyte progenitor cells co-expressing OLIG2 and CD140a/PDGFRα, and where the preparation of cells is derived from pluripotential cells derived from peripheral blood.

Another aspect of the present invention is directed to a preparation of CD140a/PDGFRα positive cells where the preparation comprises oligodendrocyte progenitor cells co-expressing OLIG2 and CD140a/PDGFRα, and where the preparation of cells is derived from pluripotential cells derived from bone marrow.

Another aspect of the present invention is directed to a preparation of cells at least 95% of which are CD140a/PDGFRα positive cells, where the preparation comprises oligodendrocyte progenitor cells co-expressing OLIG2 and CD140a/PDGFRα, and where the oligodendrocyte progenitor cells retain one or more epigenetic markers of a differentiated somatic cell other than an oligodendrocyte.

Another aspect of the present invention is directed to a method of producing an enriched preparation of oligodendrocyte progenitor cells. This method involves culturing a population of induced pluripotent stem cells under conditions effective for the cells to form embryoid bodies, and inducing cells of the embryoid bodies to differentiate into neuroepithelial cells and form neuroepithelial cell colonies. The method further involves exposing the neuroepithelial cell colonies to conditions effective to induce differentiation to oligodendrocyte progenitor cells, thereby forming an enriched preparation of oligodendrocyte progenitor cells co-expressing OLIG2 and CD140α/PDGFRα.

Another aspect of the present invention is directed to a method of treating a subject having a condition mediated by a loss of myelin or a loss of oligodendrocytes that involves administering to the subject any one of the cell preparations of the present invention under conditions effective to treat the condition.

To date a robust protocol for the scalable production of enriched and/or purified preparation of myelinogenic oligodendrocytes from induced pluripotential cells (iPSCs) has not been reported. Pouya et al., "Human Induced Pluripotent Stem Cells Differentiation into Oligodendrocyte Progenitors and Transplantation in a Rat Model of Optic Chiasm Demyelination," *PLoS ONE* 6(11):e27925 (2011) ("Pouya"), which is hereby incorporated by reference in its entirety, reports the production of human iPSc-derived oligodendrocyte progenitor cells; however the embryonic stem cell based differentiation protocol utilized by Pouya was not tailored to specifically and controllably direct neural progenitor cell differentiation followed by oligodendrocyte progenitor cell production. The lack of controlled differentiation in Pouya's protocol results in random differentiation and the generation of a heterogenous cell preparation contaminated with pluripotent cell types (e.g., Oct4, SOX2 expressing cells), not fully differentiated cell types (e.g., Pax6 and Tuj1 expressing cells), and differentiated non-oligodendrocyte progenitor cell types (e.g., neurons, astrocytes, as well as non-neural cell types). Additionally, because of random differentiation, cell sorting or selection techniques based on a single marker such as CD140a/PDGFRα, which is only specific for oligodendrocyte progenitor cells within a mixed population of brain cells but not a mixed population of non-brain cells, cannot be used to reliably enrich or purify the desired oligodendrocyte progenitor cells from Pouya's preparation. Accordingly, the preparation of Pouya is not clinically or therapeutically useful for treating conditions arising from the loss of oligodendrocytes or loss of myelin.

As described herein, applicants have developed a robust and reliable protocol for the scalable production of highly enriched preparations of myelinogenic oligodendrocytes from skin-derived human iPSCs. As demonstrated herein, the iPSCs reliably progress through serial stages of neural progenitor, glial progenitor cell, oligodendrocyte, and astrocyte differentiation in vitro. Since random differentiation is avoided, the CD140a/PDGFRα$^+$ cells of the population are oligodendrocyte progenitor cells, which can be further purified and enriched using CD140a/PDGFRα based sorting prior to clinical use. The myelination competence of the hiPSC-derived oligodendrocyte progenitor cells of the present invention was assessed in the shiverer mouse model, a genetic model of congenital hypomyelination. These cells efficiently and robustly myelinate the hypomyelinated shiverer brain, with no evidence of either tumorigenesis or heterotopic non-glial differentiation. The transplanted animals survived significantly longer than their untreated counterparts, and the majority were frankly spared otherwise early lethality, a striking clinical rescue of a fatal hereditary disorder via an iPSC-based strategy. Accordingly, under the proper conditions, human iPSCs are a feasible and effective source of oligodendrocyte progenitor cells and their derived myelinogenic central oligodendrocytes are suitable for use as patient-specific therapeutic vectors for treating disorders of central myelin.

BRIEF DESCRIPTION OF THE DRAWINGS

FIG. 1A is schematic protocol for directed differentiation of hiPSCs into OPCs. Embryoid bodies (EBs) were differentiated from undifferentiated hiPSCs (stage 1) from DIV 0-5. EBs were then differentiated as neuroepithelial (NE) cells in neural induction media (NIM; see Materials and Methods for Examples 1-9) with bFGF. FIGS. 1B-1D show that the undifferentiated hiPSCs (stage 1) and hiPSC colonies expressed the pluripotency markers SSEA4 and OCT4. Phase contrast (FIG. 1B); SSEA4 (red) (FIG. 1C); DAPI (blue). OCT4 (green) (FIG. 1D); DAPI (blue). Erythroid bodies (EBs) (FIG. 1E) and neuroepithelial cells (FIGS. 1F and 1G) could be generated from hiPSCs (stages 2 and 3). hiPSC-derived neuroepithelial cells at this stage expressed the neuroepithelial markers PAX6 and SOX1. Phase contrast (FIG. 1E); PAX6 (green) (FIG. 1F); SOX1 (red) (FIG. 1G). FIGS. 1H and 1I demonstrate that OLIG2$^+$ and NKX2.2$^-$ early glial progenitor cells appeared under the influence of retinoic acid (RA) and purmorphamine, a small-molecule agonist of sonic hedgehog signaling. By stage 4, OLIG2 was expressed in early pre-OPCs, which then serially developed NKX2.2 expression. OLIG2 (red) (FIG. 1H); NKX2.2 (green) (FIG. 1I). FIG. 1J show OLIO2$^+$/NKX2.2 early pre-OPCs were differentiated into later-stage OLIG2$^+$/NKX2.2$^+$ pre-OPCs when RA was replaced by bFGF at stage 5. OLIG2 (red); NKX2.2 (green). FIG. 1K-1M show that pre-OPCs were further differentiated into bipotential OPCs in glial induction media (GIM; see Materials and Methods for Examples 1-9) supplemented with PDGF-AA, T3, NT3, and IGF. Stage 6 was extended as long as 3-4 months for maximization of the production of myelinogenic OPCs. By the time of transplant, these cells expressed not only OLIG2 and NKX2.2 (FIG. 1K), but also SOX10 (FIG. 1L) and PDGFRα (FIG. 1M). By the end of stage 6, hiPSC OPCs could be identified as OLIG2$^+$/NKX2.2$^+$/SOX10$^+$/PDGFRα$^+$. OLIG2 (red), NKX2.2 (green) (FIG. 1K); SOX10 (red), NKX2.2 (green) (FIG. 1L); PDGFRα (red), OLIG2 (green) (FIG. 1M). FIG. 1N-1P shows in vitro terminal differentiation of hiPSC OPCs into hiPSC-derived oligodendrocytes (hiOLs), identified by O4$^+$ (FIG. 1N) and MBP$^+$ (FIG. 1O). OLs and GFAP$^+$ astrocytes (FIG. 1P) arose with reduction in glial mitogens. O4 (green). (FIG. 1N); MBP (red) (FIG. 1O); GFAP (green) (FIG. 1P); DAPI (blue). Scale: 100 μm (FIGS. 1B-1N, 1P) and 25 μm (FIG. 1O).

FIG. 3A shows the expression of neural markers during induction of oligodendroglial-lineage hiPSC-derived neuroepithelial cells in stage 3, pre-OPCs in stages 4 and 5, and OPCs in stage 6. Cultures were immunostained for PAX6 and SOX1, or OLIG2 and NKX2.2, respectively. The proportion of immunopositive clusters for each marker set were scored for each hiPSC line. At least three repeats in each group were performed; data are provided as means±SEM. In stage 6, gliogenic clusters were dissociated to single-cell suspensions and plated in GIM, resulting in the terminal differentiation of both astrocytes and myelinogenic OLs. FIGS. 3B and 3C demonstrate that GFAP$^+$ astrocytes were evident in cultures of hiPSC OPCs by 95 DIV; C27-derived (FIG. 3B) and K04-derived (FIG. 3C) astrocytes are shown here. FIG. 3D is a graph showing the proportion of GFAP$^+$ astrocytes among all cultured cells at 95 DIV; the remainder expressed oligodendroglial lineage markers (means±SEM; see FIG. 4I). ICC, immunocytochemistry. FIGS. 3E-3J are images taken later in stage 6 (160 DIV), hiPSC-derived OPCs differentiated as both O4$^+$ (FIGS. 3E and 3F) and MBP$^+$ (FIG. 3G) OLs. FIGS. 3H-3J show that when cocultured with human fetal cortical neurons, hiPSC OPCs derived from C27 (FIG. 3H), C14 (FIG. 3I), and K04 (FIG. 3J) hiPSCs all generated MBP$^+$ myelinogenic OLs that engaged NF$^+$ axons (MBP, red; NF, green). Scale: 50 μm.

FIG. 4A shows that neuroepithelial cells could be efficiently induced from both the keratinocyte-derived K04 hiPSC line and the fibroblast-derived C14 and C27 hiPSC lines. By stage 3, neural stem cells were evident and organized in rosette-like structures, and co-expressed the proneural markers, PAX6 and SOX1 (panel of cell image labeled FIG. 4A). FIGS. 4B-4C show early (Stage 4; FIG. 4B) pre-OPCs and later (Stage 5: FIG. 4C) OPCs could be induced from all 3 hiPSC (C14, C27 and K04) lines tested, as well as from H9 hESC (WA09) cells. By Stage 4, most hiPSC- or hESC-derived pre-OPCs expressed OLIG2; fewer expressed NKX2.2. By Stage 5, more NKX2.2$^+$ pre-OPCs appeared, such that double-labeled OLIG2$^+$/NKX2.2$^+$ cells typically comprised 70-90% of all DAPI$^+$ cells in each line assessed. FIGS. 4D-4H show that neuroepithelial cells from each hiPSC and hESC line could be reliably differentiated into OLIG2$^+$/NKX2.2$^+$/SOX10$^+$ OPCs. FIGS. 4E-4F are single color splits of FIG. 4D. FIG. 4I is a bar graph showing the proportions of OLIG2, NKX2.2 or SOX10 expressing OPCs quantified in K04 iPSC OPCs at stage 6. Scale: FIGS. 4A-4H, 50 μm. FIGS. 4J-4M are bar graphs showing that oligodendrocyte progenitor differentiation occurred concurrently with depletion of transcripts associated with pluripotentiality including OCT4 (FIG. 4J), hTERT (FIG. 4K), OLIG2 (FIG. 4L) or NKX2.2 (FIG. 4M). mRNAs from undifferentiated (stage 1) hiPSCs were compared to those extracted from differentiated (stage 6) iPSC hOPCs, derived from C27, K04 and WA9/H9 cells. Whereas by stage 6 both OCT4 and hTERT transcripts were significantly down-regulated in hiPSC OPCs, the pro-oligodendroglial transcripts OLIG2 and NKX2.2 were significantly up-regulated. Data are represented as means±SEM.

As shown in FIG. 5A, hiPSC OPC-derived OLs were recognized and isolated by FACS using monoclonal antibody O4, which recognizes oligodendrocytic sulfatide. The incidence of O4$^+$ oligodendroglia varied across different hiPSC lines, from 4% to 12% (see Table 3; n=4-7 experiments). FIG. 5B shows that OPCs derived from hiPSCs (C27 and K04) were readily recognized with the cell-surface marker A2B5. FIG. 5C shows that OPCs derived from either hiPSCs (C27 and K04) or hESCs (WA09/H9) were readily recognized with cell-surface markers, PDGFRα (CD140a), and CD9 by FACS analysis. The relative proportions of CD140a, CD9, and CD140a/CD9 double-labeled cells varied across the different cell-line-derived OPCs (n=4-7 experiments).

FIGS. 7A, 7G, and 7J show abundant, donor-derived MBP expression (green) by C27, K04, and C14 hiPSC OPCs (hNA, red), respectively. Representative z stacks of individual hNA$^+$ OLs are shown as asterisks in (FIGS. 7A and 7E). By the 19 week time point assessed here, C27 (FIG. 7B), K04 (FIGS. 7F and 7G), and C14 (FIG. 7J) hiPSC oligodendroglia robustly myelinated axons (NF, red). hiPSC-derived oligodendroglial morphologies are exemplified in FIG. 7F (K04) and FIG. 7I (C14); FIG. 7F shows multiaxon myelination by single OLs in the striatum. hiPSC OPCs also generated astroglia (FIG. 7C, C27; FIG. 7H, K04), which exhibited the complex fibrous morphologies typical of human astrocytes (human-specific GFAP, green). Many cells also remained as progenitors, immunostaining for NG2 (FIG. 7D, C27) and human-specific PDGFRα (FIG. 7K, C14). Scale: 50 μm (FIG. 7A-7C, 7G, 7J); 20 μm (FIGS. 7C-7F, 7H, 7K); and 10 μm (FIG. 7I, insets to 7A and 7E).

FIG. 8A is a dot map indicating the distribution of hiPSC-derived donor cells (C27) at 7 months of age, following neonatal engraftment in a shiverer mouse brain. Widespread dispersal and chimerization by hiPSC OPCs is evident (hNA, red). FIG. 8B shows hiPSC-OPC-derived myelination in a shiverer forebrain at 7 months; section 1 mm lateral to section of FIG. 8A. MBP immunoreactivity (green) is all donor derived. FIGS. 8C and 8D show myelination in sagittal sections taken at different mediolateral levels from two additional 7-month-old mice, each engrafted with C27 hiPSC OPCs at birth. FIG. 8E is a Kaplan-Meier plot showing the survival of C27 iPSC-OPC-implanted (n=22) versus saline-injected (n=19) control mice. Remaining engrafted mice sacrificed for electron microscopy at 9-10 months (≥270 days). Scale: 2 mm (FIGS. 8A and 8B).

FIGS. 10D-10G show higher-power images of donor-derived myelin in the corpus callosum, also at 40 weeks. FIGS. 10D and 10E show that the alternating major dense (arrowheads) and intraperiod lines, characteristic of mature myelin, are evident. In FIGS. 10F and 10G, myelin sheaths in the corpus callosum ensheathing central axons are shown, their maturation manifested by parallel arrays of tight junctions (FIG. 10F, arrowhead) and major dense lines (FIG. 10G, arrowhead). This mature myelination permitted the organization of architecturally appropriate nodes of Ranvier by hiPSC oligodendroglia. In FIG. 10H and FIG. 10I, nodal reconstitution in transplanted shiverers is demonstrated by immunostaining of oligodendrocytic paranodal Caspr protein (red), seen flanking nodes of Ranvier identified here by βIV spectrin (green). An isolated node is shown in confocal cross-section in FIG. 10I. Scale: 200 nm (FIG. 10A-10E); 100 nm (FIGS. 10F and 10G); and 5 μm (FIGS. 10H and 10I).

FIGS. 11C and 11D are electron micrographs of the callosum of transplanted (FIG. 11C) and untreated (FIG. 11D) shiverer brain. FIG. 11E is a lower magnification view of untransplanted shiverer white matter; same animal as shown in FIG. 11D. Scale: FIGS. 11A-11B, 10 μm; FIGS. 11C-11D, 500 nm; FIG. 11E, 1 μm.

DETAILED DESCRIPTION OF THE INVENTION

Figures 1A, 1P:
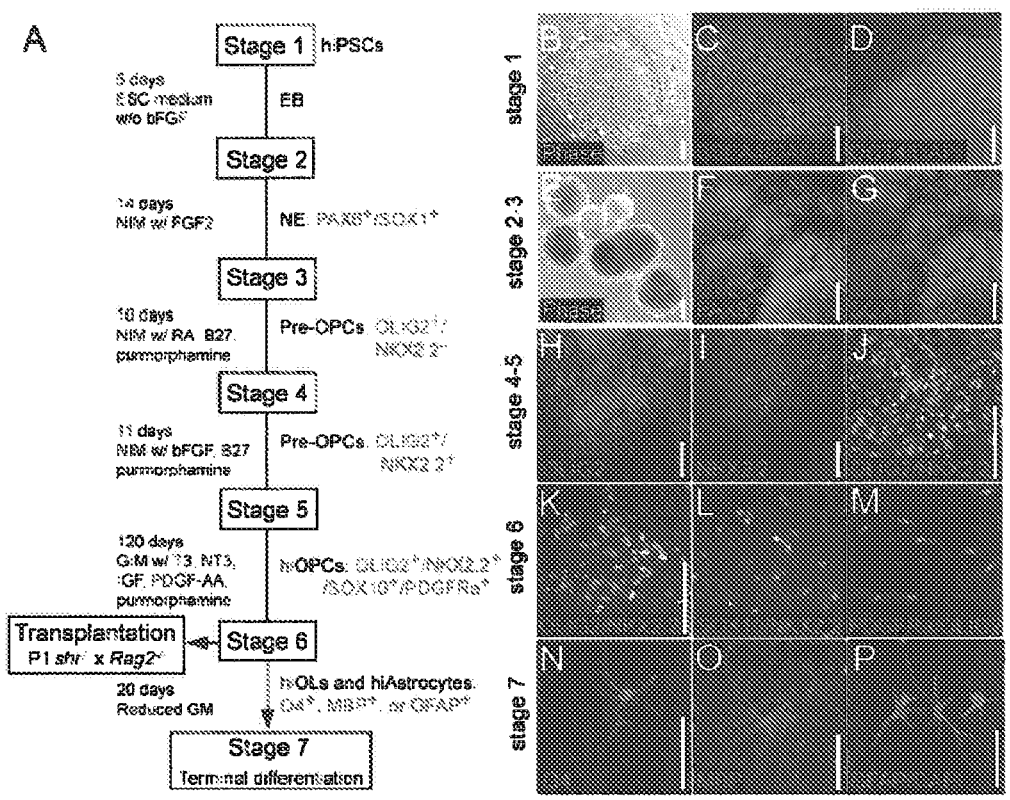
FIGS. 1A-1P show that human iPSCs (hiPSCs) can be directed into oligodendrocyte progenitor cell (OPC) fate.

The present invention is directed to preparations of CD140a/PDGFRα positive cells where the preparation comprises oligodendrocyte progenitor cells co-expressing OLIG2 and CD140a/PDGFRα. In one aspect of the present invention, the preparation of cells is derived from pluripotential cells that are derived from skin cells. In another aspect of the present invention, the preparation of cells is derived from pluripotential cells that are derived from umbilical cord blood. In another aspect of the present invention, the preparation of cells is derived from pluripotential cells that are derived from peripheral blood. In another aspect of the present invention, the preparation of cells is derived from pluripotential cells that are derived from bone marrow.

Oligodendrocyte progenitor cells, as referred to herein, comprise a population of bipotential progenitor cells that can give rise to both oligodendrocytes and astrocytes.

As described herein, the preparation of CD140a/PDGFRα positive cells are derived from pluripotential cells using a robust and scalable protocol that directs a controlled differentiation process. In one embodiment of the present invention, the pluripotential cells are induced pluripotent stem cells (iPSC). "Induced pluripotent stem cells" as used herein refers to pluripotent cells that are derived from non-pluripotent cells, such as somatic cells or tissue stem cells. For example, and without limitation, iPSCs can be derived from adult fibroblasts (see e.g., Streckfuss-Bomeke et al., "Comparative Study of Human-Induced Pluripotent Stem Cells Derived from Bone Marrow Cells, Hair Keratinocytes, and Skin Fibroblasts," *Eur. Heart J.* doi: 10.1093/eurheartj/ehs203 (2012), which is hereby incorporated by reference in its entirety), umbilical cord blood (see e.g., Cai et al., "Generation of Human Induced Pluripotent Stem Cells from Umbilical Cord Matrix and Amniotic Membrane Mesenchymal Cells," *J. Biol. Chem.* 285(15): 112227-11234 (2110) and Giorgetti et al., "Generation of Induced Pluripotent Stem Cells from Human Cord Blood Cells with only Two Factors: Oct4 and Sox2," *Nature Protocols,* 5(4):811-820 (2010), which are hereby incorporated by reference in their entirety), bone marrow (see e.g., Streckfuss-Bomeke et al., "Comparative Study of Human-Induced Pluripotent Stem Cells Derived from Bone Marrow Cells, Hair Keratinocytes, and Skin Fibroblasts," *Eur. Heart J.* doi: 10.1093/eurheartj/ehs203 (Jul. 12, 2012), and Hu et al., "Efficient Generation of Transgene-Free Induced Pluripotent Stem Cells from Normal and Neoplastic Bone Marrow and Cord Blood Mononuclear Cells," *Blood* doi: 10.1182/blood-2010-07-298331 (Feb. 4, 2011) which are hereby incorporated by reference in their entirety), and peripheral blood (see e.g., Sommer et al., "Generation of Human Induced Pluripotent Stem Cells from Peripheral Blood using the STEMCCA Lentiviral Vector," *J. Vis. Exp.* 68: e4327 doi:10.3791/4327 (2012), which is hereby incorporated by reference in its entirety). iPSCs can also be derived from keratinocytes, mature B cells, mature T cells, pancreatic β cells, melanocytes, hepatocytes, foreskin cells, cheek cells, lung fibroblasts, myeloid progenitors, hematopoietic stem cells, adipose-derived stem cells, neural stem cells, and liver progenitor cells. Methods of generating iPSCs from non-pluripotent cells are described in more detail herein.

Within the brain, PDGFRα is highly and specifically expressed by oligodendrocyte progenitor cells (Sim et al., "CD140a Identifies a Population of Highly Myelinogenic Migration-Competent and Efficiently Engrafting Human Oligodendrocyte Progenitor Cells," *Nat. Biotech.* 29(10): 934-941 (2011), which is hereby incorporated by reference in its entirety). CD140a is an ectodomain of the PDGFRα that can be readily detected and, therefore, serves as a reliable indicator or marker of PDGFRα expression. Thus, PDGFRα positive cells can be identified by CD140a and a population of PDGFRα cells can be enriched using CD140a. Such cells are referred to as PDGFα$^+$/CD140a$^+$ cells.

While PDGFRα is a highly specific marker of oligodendrocyte progenitor cells within a population of brain-derived cells, PDGFRα is expressed by a number of cells outside of the brain, and, therefore, does not constitute an oligodendrocyte specific marker in the context of a mixed population of cells containing both brain and non-brain cell types. Due to the pluripotent nature of iPSCs and possible random differentiation of these cells, the use of more than one oligodendrocyte marker is desirable for accurate identification of oligodendrocyte progenitor cells within a preparation of cells derived from iPSCs. Accordingly, the oligodendrocyte progenitor cells of the various cell preparations of the present invention are identified by their co-expression of CD140a/PDGFRα and oligodendrocyte transcription factor 2 (OLIG2). In some embodiments of the present invention, the oligodendrocyte progenitor cells of the preparation are further or alternatively identified by co-expression of one or more other oligodendrocyte progenitor cell markers such as SOX10, CD9, NKX2.2, or any combination thereof (see e.g., U.S. Patent Publication No. 2011/0059055 to Goldman et al., which is hereby incorporated by reference in its entirety).

The CD140a/PDGFRα/OLIG2 oligodendrocyte progenitor cell fraction of a preparation of the present invention may constitute greater than 30% of the preparation. In another embodiment of the present invention, the oligodendrocyte progenitor cell fraction of the preparation constitutes greater than 40% of the preparation. In other embodiments of the present invention, the oligodendrocyte progenitor cell fraction of the preparation constitutes >45% of the preparation, >50% of the preparation, >55% of the preparation, >60% of the preparation, >65% of the preparation, >70% of the preparation, >75% of the preparation, >80% of the preparation, or >90% of the preparation.

Another aspect of the present invention relates to a preparation of cells that has been enriched for oligodendrocyte progenitor cells. This aspect of the present invention is directed to a preparation of cells, at least 95% of which are CD140a/PDGFRα positive cells, where the preparation comprises oligodendrocyte progenitor cells co-expressing OLIG2 and CD140a/PDGFRα, and where the oligodendrocyte progenitor cells retain one or more epigenetic markers of a differentiated somatic cell other than an oligodendrocyte. In one embodiment of the present invention, greater than 95% of the cells in the preparation are CD140a/PDGFRα positive cells. In another embodiment of the present invention, greater than 98% of the cells in the preparation are CD140a/PDGFRα positive cells. In one embodiment of this aspect of the present invention, at least 90% of the cell preparation comprises oligodendrocyte progenitor cells. In another embodiment of this aspect of the present invention, at least 95% of the cell preparation comprises oligodendrocyte progenitor cells.

The cell preparations of the present invention are preferably substantially free of non-oligodendrocyte progenitor cell contaminants. In particular, preparations of CD140a/PDGFRα positive cells are substantially free (e.g., containing less than 20%, 15%, 10%, 9%, 8%, 7%, 6%, 5%, 4%, 3%, 2%, or 1%) of other neural cell types such as astrocytes (e.g., GFAP antibody defined cells), neurons (e.g., MAP2 and PSA-NCAM antibody defined cells), microglia (e.g., CD11, CD32, and CD36 antibody defined cells), or non-brain cell types. The cell preparations of the present invention containing oligodendrocyte progenitor cells are also substantially free (e.g., containing less than 20%, 15%, 10%, 9%, 8%, 7%, 6%, 5%, 4%, 3%, 2%, or 1%) of non-differentiated, residual pluripotent cell types, e.g., the preparation is substantially free of cells expressing either OCT4, NANOG, or SSEA4, and is substantially free of less differentiated cell lineages, e.g., neural progenitor cells identified by PAX6 and/or TUJ1 expression.

In one embodiment of the present invention, the cells of the preparation of the present invention are mammalian cells, including, for example, but without limitation, human, monkey, rat, or mouse cells.

The cell preparations of the present invention, and in particular, the oligodendrocyte progenitor cell populations of the present invention can be structurally distinguished from tissue derived or embryonic stem cell-derived oligodendrocyte progenitor cell counterparts based on the maintenance of one or more epigenetic markers of its somatic cell origin. For example, when the iPSCs are derived from skin cells such as dermal fibroblasts, the iPSC-derived oligodendrocyte progenitor cells maintain one or more epigenetic markers of a somatic skin cell. The one or more epigenetic markers may include, without limitation, methylation marks (e.g., DNA and/or RNA methylation markers), or a histone modification (e.g., acetylation, methylation, ubiquitylation, phosphorylation, or sumoylation).

The oligodendrocyte progenitor cell preparations of the present invention are functionally distinguishable from their tissue derived or embryonic stem cell-derived oligodendrocyte progenitor cell counterparts. As demonstrated herein the cell preparations of the present invention have an in vivo myelination efficiency that is greater than the in vivo myelination efficiency of a preparation of A2B5$^+$/PSA-NCAM$^-$ or CD140a$^+$ sorted fetal human tissue derived oligodendrocyte progenitor cells. Myelination efficiency is measured by the proportion of central axons myelinated as a function of time after engraftment. As demonstrated herein, the cell preparations of the present invention are also capable of achieving an in vivo myelination density upon engraftment which is greater than that achievable with a preparation of A2B5$^+$/PSA-NCAM$^-$ or CD140a$^+$ sorted fetal human tissue derived oligodendrocyte progenitor cells. Additionally, the cell preparations of the present invention are capable, upon engraftment, of achieving improved survival in a myelination deficient mammal compared to that achievable with a preparation of A2B5$^+$/PSA-NCAM$^-$ or CD140a$^+$ sorted fetal human tissue derived oligodendrocyte progenitor cells. In other words, the proportion of myelination deficient mammals surviving at any given timepoint is greater in iPSC oligodendrocyte progenitor engrafted mammals than fetal human tissue derived A2B5$^+$/PS-NCAM$^-$ cell engrafted mammals that had otherwise been treated identically. For example, only ~25% of animals engrafted with fetal tissue derived oligodendrocyte progenitor cells survive beyond 6 months of age, whereas 50% of animals engrafted with iPSC-derived oligodendrocyte progenitor cells survive beyond 6 months. Accordingly, the oligodendrocyte progenitor cell preparations of the present invention are functionally distinguishable from non-iPSC derived oligodendrocyte progenitor cell preparations.

The cell preparations of the present invention, including the CD140a/PDGFRα enriched preparations can be optionally expanded in culture to increase the total number of cells. The cells can be expanded by either continuous or pulsatile exposure to PDGF-AA or AB as mitogens that support the expansion of oligodendrocyte progenitor cells; they can be exposed to fibroblast growth factors, including FGF2, FGF4, FGF8, and FGF9, which can support the mitotic expansion of the glial progenitor cells, but which can bias their differentiation to a mixed population of astrocytes as well as oligodendrocytes. The cells can also be expanded in media supplemented with combinations of FGF2, PDGF, and NT3, which can optionally be supplemented with either platelet-depleted or whole serum (see Nunes et al. "Identification and Isolation of Multipotent Neural Progenitor Cells from the Subcortical White Matter of the Adult Human Brain," *Nature Medicine* 9:239-247; Windrem et al., "Fetal and Adult Human Oligodendrocyte Progenitor Cell Isolates Myelinate the Congenitally Dysmyelinated Brain," *Nature Medicine* 10:93-97 (2004), which are incorporated by reference for the methods and compositions described therein).

The populations of oligodendrocyte progenitor cells are optionally genetically modified to express one or more proteins of interest. For example, the cells can be modified to express an exogenous targeting moiety, an exogenous marker (for example, for imaging purposes), or the like. The oligodendrocyte progenitor cells of the cell preparations of the present invention can be optionally modified to overexpress an endogenous targeting moiety, marker, or a myelin basic protein, or the like.

Another aspect of the present invention is directed to a method of producing an enriched preparation of oligodendrocyte progenitor cells. This method involves culturing a population of induced pluripotent stem cells under conditions effective for the cells to form embryoid bodies, and inducing cells of the embryoid bodies to differentiate into neuroepithelial cells and form neuroepithelial cell colonies. The method further involves exposing the neuroepithelial cell colonies to conditions effective to induce differentiation to oligodendrocyte progenitor cells, thereby forming an enriched preparation of oligodendrocyte progenitor cells co-expressing OLIG2 and CD140a/PDGFRα. The enriched preparation of oligodendrocyte progenitor cells may further express SOX10, CD9 or a combination thereof.

iPSCs can be derived from any species, including but not limited to, human, non-human primates, rodents (mice, rats), ungulates (cows, sheep, etc), dogs, cats, rabbits, hamsters, goats, and the like. The iPSCs can be obtained from embryonic, fetal, newborn, and adult tissue, from peripheral blood, umbilical cord blood, and bone marrow. Exemplary somatic cells that can be used include fibroblasts, such as dermal fibroblasts obtained by a skin sample or biopsy, synoviocytes from synovial tissue, keratinocytes, mature B cells, mature T cells, pancreatic β cells, melanocytes, hepatocytes, foreskin cells, cheek cells, or lung fibroblasts. Exemplary stem or progenitor cells that are suitable for iPSC production include, without limitation, myeloid progenitors, hematopoietic stem cells, adipose-derived stem cells, neural stem cells, and liver progenitor cells. Although skin and cheek provide a readily available and easily attainable source of appropriate cells, virtually any cell can be used.

Induced pluripotent stem cells can be produced by expressing a combination of reprogramming factors in a somatic cell. Suitable reprogramming factors that promote and induce iPSC generation include one or more of Oct4, Klf4, Sox2, c-Myc, Nanog, C/EBPα, Esrrb, Lin28, and Nr5a2. In certain embodiments, at least two reprogramming factors are expressed in a somatic cell to successfully reprogram the somatic cell. In other embodiments, at least three reprogramming factors are expressed in a somatic cell to successfully reprogram the somatic cell. In other embodiments, at least four reprogramming factors are expressed in a somatic cell to successfully reprogram the somatic cell.

iPSCs may be derived by methods known in the art including the use integrating viral vectors (e.g., lentiviral vectors, inducible lentiviral vectors, and retroviral vectors), excisable vectors (e.g., transposon and floxed lentiviral vectors), and non-integrating vectors (e.g., adenoviral and plasmid vectors) to deliver the genes that promote cell reprogramming (see e.g., Takahashi and Yamanaka, *Cell* 126:663-676 (2006); Okita. et al., *Nature* 448:313-317 (2007); Nakagawa et al., *Nat. Biotechnol.* 26:101-106 (2007); Takahashi et al., *Cell* 131:1-12 (2007); Meissner et al. *Nat. Biotech.* 25:1177-1181 (2007); Yu et al. *Science* 318:1917-1920 (2007); Park et al. *Nature* 451:141-146 (2008); and U.S. Patent Application Publication No. 2008/0233610, which are hereby incorporated by reference in their entirety). Other methods for generating IPS cells include those disclosed in WO2007/069666, WO2009/006930, WO2009/006997, WO2009/007852, WO2008/118820, U.S. Patent Application Publication Nos. 2011/0200568 to Ikeda et al., 2010/0156778 to Egusa et al., 2012/0276070 to Musick, and 2012/0276636 to Nakagawa, Shi et al., *Cell Stem Cell* 3(5): 568-574 (2008), Kim et al., *Nature* 454: 646-650 (2008), Kim et al., *Cell* 136(3):411-419 (2009), Huangfu et al., *Nature Biotechnology* 26: 1269-1275 (2008), Zhao et al., *Cell Stem Cell* 3: 475-479 (2008), Feng et al., *Nature Cell Biology* 11: 197-203 (2009), and Hanna et al., *Cell* 133(2): 250-264 (2008) which are hereby incorporated by reference in their entirety.

Integration free approaches, i.e., those using non-integrating and excisable vectors, for deriving iPSCs free of transgenic sequences are particularly suitable in the therapeutic context. Suitable methods of iPSC production that utilize non-integrating vectors include methods that use adenoviral vectors (Stadtfeld et al., "Induced Pluripotent Stem Cells Generated without Viral Integration," *Science* 322: 945-949 (2008), and Okita et al., "Generation of Mouse Induced Pluripotent Stem Cells without Viral Vectors," *Science* 322: 949-953 (2008), which are hereby incorporated by reference in their entirety), Sendi virus vectors (Fusaki et al., "Efficient Induction of Transgene-Free Human Pluripotent Stem Cells Using a Vector Based on Sendi Virus, an RNA Virus That Does Not Integrate into the Host Genome," *Proc Jpn Acad.* 85: 348-362 (2009), which is hereby incorporated by reference in its entirety), polycistronic minicircle vectors (Jia et al., "A Nonviral Minicircle Vector for Deriving Human iPS Cells," *Nat. Methods* 7: 197-199 (2010), which is hereby incorporated by reference in its entirety), and self-replicating selectable episomes (Yu et al., "Human Induced Pluripotent Stem Cells Free of Vector and Transgene Sequences," *Science* 324: 797-801 (2009), which is hereby incorporated by reference in its entirety). Suitable methods for iPSC generation using excisable vectors are described by Kaji et al., "Virus-Free Induction of Pluripotency and Subsequent Excision of Reprogramming Factors," *Nature* 458: 771-775 (2009), Soldner et al., "Parkinson's Disease Patient-Derived Induced Pluripotent Stem Cells Free of Viral Reprogramming Factors," *Cell* 136:964-977 (2009), Woltjen et al., "PiggyBac Transposition Reprograms Fibroblasts to Induced Pluripotent Stem Cells," *Nature* 458: 766-770 (2009), and Yusa et al., "Generation of Transgene-Free Induced Pluripotent Mouse Stem Cells by the PiggyBac Transposon," *Nat. Methods* 6: 363-369 (2009), which are hereby incorporated by reference in their entirety. Suitable methods for iPSC generation also include methods involving the direct delivery of reprogramming factors as recombinant proteins (Zhou et al., "Generation of Induced Pluripotent Stem Cells Using Recombinant Proteins," *Cell Stem Cell* 4: 381-384 (2009), which is hereby incorporated by reference in its entirety) or as whole-cell extracts isolated from ESCs (Cho et al., "Induction of Pluripotent Stem Cells from Adult Somatic Cells by Protein-Based Reprogramming without Genetic Manipulation," *Blood* 116: 386-395 (2010), which is hereby incorporated by reference in its entirety).

The methods of iPSC generation described above can be modified to include small molecules that enhance reprogramming efficiency or even substitute for a reprogramming factor. These small molecules include, without limitation, epigenetic modulators such as the DNA methyltransferase inhibitor 5'-azacytidine, the histone deacetylase inhibitor VPA, and the G9a histone methyltransferase inhibitor BIX-01294 together with BayK8644, an L-type calcium channel agonist. Other small molecule reprogramming factors include those that target signal transduction pathways, such as TGF-β inhibitors and kinase inhibitors (e.g., kenpaullone) (see review by Sommer and Mostoslaysky, "Experimental Approaches for the Generation of Induced Pluripotent Stem Cells," *Stem Cell Res. Ther.* 1:26 doi:10.1186/scrt26 (Aug. 10, 2010), which is hereby incorporated by reference in its entirety).

Suitable iPSCs derived from adult fibroblasts can be obtained following the procedure described in Streckfuss-Bomeke et al., "Comparative Study of Human-Induced Pluripotent Stem Cells Derived from Bone Marrow Cells, Hair Keratinocytes, and Skin Fibroblasts," *Eur. Heart J. doi:* 10.1093/eurheartj/ehs203 (2012), which is hereby incorporated by reference in its entirety). iPSCs derived from umbilical cord blood cells can be obtained as described in Cai et al., "Generation of Human Induced Pluripotent Stem Cells from Umbilical Cord Matrix and Amniotic Membrane Mesenchymal Cells," *J. Biol. Chem.* 285(15): 112227-11234 (2110) and Giorgetti et al., "Generation of Induced Pluripotent Stem Cells from Human Cord Blood Cells with only Two Factors: Oct4 and Sox2," *Nature Protocols,* 5(4):811-820 (2010), which are hereby incorporated by reference in their entirety. iPSCs derived from bone marrow cells can be obtained using methods described in Streckfuss-Bomeke et al., "Comparative Study of Human-Induced Pluripotent Stem Cells Derived from Bone Marrow Cells, Hair Keratinocytes, and Skin Fibroblasts," *Eur. Heart J. doi:* 10.1093/eurheartj/ehs203 (Jul. 12, 2012), and Hu et al., "Efficient Generation of Transgene-Free Induced Pluripotent Stem Cells from Normal and Neoplastic Bone Marrow and Cord Blood Mononuclear Cells," *Blood* doi: 10.1182/blood-2010-07-298331 (Feb. 4, 2011) which are hereby incorporated by reference in their entirety). iPSCs derived from peripheral blood can be obtained following the methods described in Sommer et al., "Generation of Human Induced Pluripotent Stem Cells from Peripheral Blood using the STEMCCA Lentiviral Vector," *J. Vis. Exp.* 68: e4327 doi: 10.3791/4327 (2012), which is hereby incorporated by reference in its entirety. iPS cells contemplated for use in the methods of the present invention are not limited to those described in the above references, but rather includes cells prepared by any method as long as the cells have been artificially induced from cells other than pluripotent stem cells.

As described herein and shown in FIG. 1A, oligodendrocyte progenitor cells can be derived from iPSCs using a protocol that directs the iPSCs through serial stages of neural and glial progenitor cell differentiation. Each stage of lineage restriction is characterized and identified by the expression of certain cell proteins.

With reference to FIG. 1A, Stage 1 of the process involves culturing iPSCs under conditions effective to induce embryoid body formation. As described herein, iPSCs may be maintained in co-culture with other cells, such as embryonic fibroblasts, in an embryonic stem cell (ESC) media (e.g., DMEM/F12 containing a suitable serum replacement and bFGF). The iPSCs are passaged before reaching 100% confluence, e.g., 80% confluence, when colonies are approximately 250-300 µm in diameter. The pluripotential state of the cells can be readily assessed using markers to SSEA4, TRA-1-60, OCT-4, NANOG, and/or SOX2.

To generate embryoid bodies (EBs) (Stage 2), which are complex three-dimensional cell aggregates of pluripotent stem cells, iPSC cultures are dissociated once they achieved ~80% confluence with colony diameters at or around 250-300 µm. The EBs are initially cultured in suspension in ESC media without bFGF, and then switched to neural induction medium supplemented with bFGF and heparin. To induce neuroepithelial differentiation (Stage 3), EBs are plated and cultured in neural induction medium supplemented with bFGF, heparin, laminin, then switched to neural induction media supplemented with retinoic acid. Neuroepithelial differentiation is assessed by the co-expression of PAX6 and SOX1, which characterize central neural stem and progenitor cells.

To induce pre-oligodendrocyte progenitor cell ("pre-OPCs") differentiation, neuroepithelial cell colonies are cultured in the presence of additional factors including retinoic acid, B27 supplement, and a sonic hedgehog (shh) agonist (e.g., purmophamine). The appearance of pre-OPC colonies can be assessed by the presence of OLIG2 and/or NKX2.2 expression. While both OLIG2 and NKX2.2 are expressed by central oligodendrocyte progenitor cells, NKX2.2 is a more specific indicator of oligodendroglial differentiation. Accordingly, an early pre-oligodendrocyte progenitor cell stage is marked by OLIG$^+$/NKX2.2$^-$ cell colonies. OLIG$^+$/NKX2.2$^-$ early pre-OPCs are differentiated into later-stage OLIG$^+$/NKX2.2$^+$ pre-OPCs by replacing retinoic acid with bFGF. At the end of Stage 5, a significant percentage of the cells are pre-OPCs as indicated by OLIG2$^+$/NKX2.2$^+$ expression profile.

Pre-OPCs are further differentiated into bipotential oligodendrocyte progenitor cells by culture in glial induction media supplemented with growth factors such as triiodothyronine (T3), neurotrophin 3 (NT3), insulin growth factor (IGF-1), and platelet-derived growth factor-AA (PDGF-AA) (Stage 6). These culture conditions can be extended for 3-4 months or longer to maximize the production of myelinogenic oligodendrocyte progenitor cells. Cell preparations suitable for therapeutic transplant are identified as containing OLIG2$^+$/NKX2.2$^+$/SOX10$^+$/PDGFRα$^+$ oligodendrocyte progenitor cells. In vitro terminal differentiation of oligodendrocyte progenitor cells into oligodendrocytes, identified by O4$^+$ and myelin basic protein (MBP), arose in further culture with a reduction of glial mitogens.

In some embodiments of the present invention, it may be preferable to enrich for oligodendrocyte progenitor cells within a cell preparation produced using the methods described herein. Accordingly, in one embodiment, selection of CD140a/PDGFRα positive cells is employed to produce a purified or enriched preparation of oligodendrocyte progenitor cells. In another embodiment of the present invention, selection of CD9 positive cells is employed to produce a purified or enriched preparation of oligodendrocyte progenitor cells. In yet another embodiment, both CD140a/PDGFRα and CD9 positive cell selection is employed to produce a purified or enriched preparation of oligodendrocyte progenitor cells.

Selection for a PDGFRα marker and/or a CD9 marker can be carried out serially or sequentially and can be performed using conventional methods known in the art such as immunopanning. The selection methods optionally involve the use of fluorescence sorting (FACS), magnetic sorting (MACS)

or any other methods that allow a rapid, efficient cell sorting. Examples of methods for cell sorting are taught for example in U.S. Pat. No. 6,692,957, which is hereby incorporated by reference in its entirety.

Generally, cell sorting methods use a detectable moiety. Detectable moieties include any suitable direct or indirect label, including, but not limited to, enzymes, fluorophores, biotin, chromophores, radioisotopes, colored beads, electrochemical, chemical-modifying or chemiluminescent moieties. Common fluorescent moieties include fluorescein, cyanine dyes, coumarins, phycoerythrin, phycobiliproteins, dansyl chloride, Texas Red, and lanthanide complexes or derivatives thereof. Magnetic cell sorting may be used.

When cell sorting is performed, the marker can be an ectodomain and cell permeabilization or membrane disruption techniques are not used. By way of example, the PDGFRα marker selection step is optionally performed using an antibody or other binding moiety that binds an ectodomain of the PDGFRα (e.g. CD140a). Suitable antibodies include, but are not limited to, monoclonal and polyclonal antibodies, chimeric antibodies, antibody fragments (e.g., F(ab')2, Fab', Fab fragments) capable of binding the selected marker, and single chain antibodies. Other binding moieties include marker ligands, cofactors, and the like that specifically bind to the marker. Thus, in the case of a marker that is a receptor, a receptor ligand or binding portion thereof can be used as a detectable moiety. Antibodies and other binding moieties are commercially available or can be made using techniques available to a skilled artisan.

One of skill in the art readily appreciates how to select for or against a specific marker. Thus, by way of example, a population of cells sorted for a particular marker includes identifying cells that are positive for that particular marker and retaining those cells for further use or further selection steps. A population of cells sorted against a specific marker includes identifying cells that are positive for that particular marker and excluding those cells for further use or further selection steps.

Another aspect of the present invention is directed to a method of treating a subject having a condition mediated by a loss of myelin or a loss of oligodendrocytes. This method involves administering to the subject any one of the oligodendrocyte progenitor cell preparations of the present invention under conditions effective to treat the condition. In accordance with this aspect of the present invention, any of cell preparations described herein are suitable for therapeutic treatment.

Conditions mediated by a loss of myelin or a loss of oligodendrocytes that can be treated in accordance with the methods of the present invention include hypomyelination disorders and demyelinating disorders. In one embodiment of the present invention, the condition is an autoimmune demyelination condition, such as e.g., multiple sclerosis, neuromyelitis optica, transverse myelitis, and optic neuritis. In another embodiment of the present invention, the myelin-related disorder is a vascular leukoencephalopathy, such as e.g., subcortical stroke, diabetic leukoencephalopathy, hypertensive leukoencephalopathy, age-related white matter disease, and spinal cord injury. In another embodiment of the present invention, the myelin-related condition is a radiation induced demyelination condition. In another embodiment of the present invention, the myelin-related disorder is a pediatric leukodystrophy, such as e.g., Pelizaeus-Merzbacher Disease, Tay-Sach Disease, Sandhoff's gangliosidoses, Krabbe's disease, metachromatic leukodystrophy, mucopolysaccharidoses, Niemann-Pick A disease, adrenoleukodystrophy, Canavan's disease, Vanishing White Matter Disease, and Alexander Disease. In yet another embodiment of the present invention, the myelin-related condition is periventricular leukomalacia or cerebral palsy.

The number of oligodendrocyte progenitor cells administered to the subject can range from about $10^2$-$10^8$ cells at each transplantation (e.g., injection site), depending on the size and species of the recipient, and the volume of tissue requiring myelin production or replacement. Single transplantation (e.g., injection) doses can span ranges of $10^3$-$10^5$, $10^4$-$10^7$, and $10^5$-$10^8$ cells, or any amount in total for a transplant recipient patient.

Delivery of the cells to the subject can include either a single step or a multiple step injection directly into the nervous system. Specifically, the cells can be delivered directly to one or more sites of the brain, the brain stem, the spinal cord, and/or any combination thereof. For localized disorders such as demyelination of the optic nerve, a single injection can be used. Although the oligodendrocyte precursor cells of the present invention disperse widely within a transplant recipient's brain, for widespread demyelinating or hypomyelination disorders, multiple injections sites can be performed to optimize treatment. Injection is optionally directed into areas of the central nervous system such as white matter tracts like the corpus callosum (e.g., into the anterior and posterior anlagen), dorsal columns, cerebellar peduncles, cerebral peduncles via intraventricular, intracallosal, or intraparenchymal injections. Such injections can be made unilaterally or bilaterally using precise localization methods such as stereotaxic surgery, optionally with accompanying imaging methods (e.g., high resolution MRI imaging). One of skill in the art recognizes that brain regions vary across species; however, one of skill in the art also recognizes comparable brain regions across mammalian species.

The cellular transplants are optionally injected as dissociated cells but can also be provided by local placement of non-dissociated cells. In either case, the cellular transplants optionally comprise an acceptable solution. Such acceptable solutions include solutions that avoid undesirable biological activities and contamination. Suitable solutions include an appropriate amount of a pharmaceutically-acceptable salt to render the formulation isotonic. Examples of the pharmaceutically-acceptable solutions include, but are not limited to, saline, Ringer's solution, dextrose solution, and culture media. The pH of the solution is preferably from about 5 to about 8, and more preferably from about 7 to about 7.5.

The injection of the dissociated cellular transplant can be a streaming injection made across the entry path, the exit path, or both the entry and exit paths of the injection device (e.g., a cannula, a needle, or a tube). Automation can be used to provide a uniform entry and exit speed and an injection speed and volume.

Optionally a multifocal delivery strategy can be used, for example as described in the examples. Such a multifocal delivery strategy is designed to achieve widespread, dense, whole neuraxis donor cell engraftment throughout the recipient central nervous system. Injection sites can be chosen to permit contiguous infiltration of migrating donor cells into one or more of the major brain areas, brainstem, and spinal cord white matter tracts, without hindrance (or with limited hindrance) from intervening gray matter structures. For example, injection sites optionally include four locations in the forebrain subcortex, specifically into the anterior and posterior anlagen of the corpus callosum bilaterally, and into a fifth location in the cerebellar peduncle dorsally.

Optionally, the methods of treatment provided herein further comprise assessing remyelination directly or indirectly. For example, imagining technique, conduction velocities, or symptomatic improvement are optionally tested subsequent to engraftment.

An advantage of the oligodendrocyte progenitor cells of the present invention is the ability to obtain patient specific preparation for autologous cell therapy (i.e., the cell preparation is derived from the subject being treated). Autologous oligodendrocyte progenitor cells can be derived, for example, from the somatic skin cells, umbilical chord blood, peripheral blood, or bone marrow of the subject being treated. Oligodendrocyte progenitor cells derived from allogeneic and/or xenogeneic cell sources are also suitable for use in the methods of the present invention.

EXAMPLES

The following examples are provided to illustrate embodiments of the present invention but they are by no means intended to limit its scope Material and Methods for Examples 1-9 hESC and hiPSC Culture. Four distinct lines of pluripotent cells were used in this study. These included hESCs (WA09/H9; WiCell, Madison, Wis., USA) and hiPSCs of both keratinocyte (K04; K. Hochedlinger) and fibroblast origin (C14 and C27 hiPSCs; L. Studer). The experiments described were approved by the University of Rochester Embryonic Stem Cell Research Oversight committee.

OPC Production. OPCs were induced from hESCs and iPSCs using modifications of published protocols (Hu et al., "Human Oligodendrocytes From Embryonic Stem Cells: Conserved SHH Signaling Networks and Divergent FGF Effects," *Development* 136:1443-1452 (2009); Hu et al., "Differentiation of Human Oligodendrocytes From Pluripotent Stem Cells," *Nat. Protoc.* 4:1614-1622 (2009b); Izrael et al., "Human Oligodendrocytes Derived From Embryonic Stem Cells: Effect of Noggin on Phenotypic Differentiation in Vitro and on Myelination in Vivo," *Mol. Cell. Neurosci.* 34:310-323 (2007), which are hereby incorporated by reference in their entirety), as schematized in FIG. 1 and described in detail below.

Directed Astrocytic or Oligodendrocytic Maturation. hiPSC- or hESC-derived gliogenic spheres at 120-170 DIV were cultured in suspension in GIM supplemented with platelet-derived growth factor-AA (PDGF-AA; 10 ng/ml), insulin growth factor-1 (IGF-1; 10 ng/ml) and Neurotrophin-3 (NT3; 10 ng/ml). To differentiate these OPCs into mature oligodendrocytes (OLs) or astrocytes, the spheres were dissected into small cell clusters (around 50-100 mm in diameter) mechanically with a Sharpoint blade (Surgimed-MLB). The dissected OPC clusters were plated onto poly-ornithine/laminin-coated 12-well plates and cultured in GIM for 1-2 weeks. For induction of astrocytes, the OPC clusters were cultured either in GIM supplemented with PDGF-AA (10 ng/ml), IGF-1 (10 ng/ml), and NT3 (10 ng/ml) or in GIM supplemented with 10% fetal bovine serum (FBS; HyClone) for 1-2 weeks. For directing the maturation of OLs, the cultures were switched to half GIM supplemented with PDGF-AA (5 ng/ml), IGF-1 (5 ng/ml), and NT3 (5 ng/ml) plus half neurobasal (NB) media (Invitrogen) supplemented with B27 (1×) and brain-derived neurotrophic factor (BDNF; 10 ng/ml) and grown for 2-4 weeks. The mature astrocytes were recognized with immunostaining of anti-GFAP or anti-CD44. Oligodendroglia were identified using O4 and MBP antibodies.

Isolation of Human Fetal Neuronal Progenitor Cells for Coculture. Human fetal forebrain tissue was obtained from second-trimester aborted fetuses of 20 weeks g.a. Tissues were obtained as de-identified tissue, as approved by the Research Subjects Review Board of the University of Rochester Medical Center. The tissue samples were washed 2-3 times with sterile Hank's balanced salt solution with $Ca^{2+}/Mg^{2+}$ ($HBSS^{+/+}$). Cortical plate tissue was separated from the ventricular zone/subventricular zone, then dissociated with papain (Worthington Biochemical) as described (Keyoung et al., "High-Yield Selection and Extraction of Two Promoter-Defined Phenotypes of Neural Stem Cells From the Fetal Human Brain," *Nat. Biotechnol.* 19:843-850 (2001); Wang et al., "Prospective Identification, Isolation, and Profiling of a Telomerase-Expressing Subpopulation of Human Neural Stem Cells, Using sox2 Enhancer-Directed Fluorescence-Activated Cell Sorting," *J. Neurosci.* 30:14635-14648 (2010), which are hereby incorporated by reference in their entirety). The cells were resuspended at $2\text{-}4 \times 10^6$ cells/ml in Dulbecco's modified Eagle's medium (DMEM)/F12 supplemented with N-2 supplement (Life Technologies) and basic fibroblast growth factor (bFGF; 20 ng/ml) and plated in suspension culture dishes. A day later, the cells were recovered and neurons isolated by magnetic-activated cell sorting (Windrem et al., "Neonatal Chimerization With Human Glial Progenitor Cells Can Both Remyelinate and Rescue the Otherwise Lethally Hypomyelinated Shiverer Mouse," *Cell Stem Cell* 2:553-565 (2008), which is hereby incorporated by reference in its entirety). In brief, the recovered neural progenitor cells were incubated with PSA-NCAM (Chemicon) at 1:100 for 30 min, then washed and labeled with rat anti-mouse immunoglobulin M microbeads (Miltenyi Biotech). The bound $PSA\text{-}NCAM^+$ neurons were eluted, spun, washed with DMEM/F12, and then cultured in DMEM/F12 with N2, 0.5% PD-FBS, and bFGF (20 ng/ml) for 4-6 days. For coculture with hiPSC OPCs, the fetal cortical neurons were dissociated into single cells and then plated onto either poly-L-ornithine/laminin-coated 24-well plates or poly-L-ornithine/fibronectin coated coverslips (50,000-100,000 cells per well or coverslip). The replated neurons were then switched to NB media with B27 (1×) and BDNF (10 ng/ml; Invitrogen) for an additional 6-10 days prior to coculture.

Coculture of hiPSC-Derived OPCs with Human Fetal Cortical Neurons In Vitro. Gliogenic OPC spheres derived from either K04 or C27 hiPSCs were induced up to 130 DIV prior to coculture. These were dissected into small pieces of <1 $mm^3$ and cultured for 2-3 weeks to allow the OPCs to expand as a monolayer surrounding the core clusters. The OPC clusters and their monolayer surrounds were then recollected with cold $HBSS^{-/-}$ from the culture dishes and manually dissected into smaller fragments of 100-200 µm in diameter. Small aliquots were fully dissociated into single cells with Accutase (Chemicon) for 5 min at room temperature, then assessed by hemocytometry. For coculture, the hiPSC OPCs were then seeded at 200,000 cells/ml, either with or without human cortical neurons, and cultured in a 1:1 mixture of NB/B27/BDNF and GIM/NT3/IGF-1/PDGF-AA media. The cultures of cortical neurons alone, hiPSC OPCs alone, or both populations together were allowed to grow 2-4 additional weeks before fixation and immunolabeling for O4, MBP, GFAP, and βIII-tubulin.

RNA Extraction and RT-PCR. Total RNA was extracted from undifferentiated hESCs and hiPSCs, or hESC- and hiPSC-derived OPCs, using RNeasy mini kit (QIAGEN). The first of strand of complementary DNA was transcribed using the TaqMan Reverse Transcription kit (Roche #N808-0234). The primer sequences are provided in Table 1 below. The relative abundance of transcript expression of mRNAs was measured with the ABI PRISM 7000 system. The resultant expression data were normalized to the expression level of glyceraldehyde-3-phosphate dehydrogenase (GAPDH) mRNA. Statistical analysis was performed on transformed data. The means and SEM were calculated following a paired t test.

TABLE 1

Primers of human genes used for qRT-PCR

| Target Gene | Forward primer | Reverse primer | Accession number |
|---|---|---|---|
| c-MYC | CGTCTCCACACATCAGCACAA (SEQ ID NO: 1) | TCTTGGCAGCAGGATAGTCCT (SEQ ID NO: 2) | NM_002467.4 |
| GAPDH | CCACCCATGGCAAATTCC (SEQ ID NO: 3) | TGGGATTTCCATTGATGACAAG (SEQ ID NO: 4) | NM_002046.3 |
| GFAP | CATCGAGATCGCCACCTACA (SEQ ID NO: 5) | TCTGCACGGGAATGGTGAT (SEQ ID NO: 6) | NM_001131019.1 |
| hTERT | TGCGGCCGATTGTGAAC (SEQ ID NO: 7) | CCTCTTTTCTCTGCGGAACGT (SEQ ID NO: 8) | NM_001193376.1 |
| KLF4 | ACCAGGCACTACCGTAAACACA (SEQ ID NO: 9) | GGTCCGACCTGGAAAATGCT (SEQ ID NO: 10) | NM_004235.4 |
| NANOG | CCAAAGGCAAACAACCCACTT (SEQ ID NO: 11) | TCTTGACCGGGACCTTGTCT (SEQ ID NO: 12) | NM_024865.2 |
| NKX2.2 | GGCGGGCATTCCCTTTT (SEQ ID NO: 13) | CGAGCTGTACTGGGCGTTGT (SEQ ID NO: 14) | NM_002509.3 |
| OCT4 | TGGTCCGAGTGTGGTTCTGTAA (SEQ ID NO: 15) | TGTGCATAGTCGCTGCTTGAT (SEQ ID NO: 16) | NM_001173531.1 |
| OLIG2 | GGCGCGCAACTACATCCT (SEQ ID NO: 17) | CGCTCACCAGTCGCTTCAT (SEQ ID NO: 18) | NM_005806.2 |
| PAX6 | TCGGGCACCACTTCAACAG (SEQ ID NO: 19) | TCCGGGAACTTGAACTGGAA (SEQ ID NO: 20) | NM_000280.3 |
| PDGFR | CCTTGGTGGCACCCCTTAC (SEQ ID NO: 21) | TCCGGTACCCCACTCTTGATCT (SEQ ID NO: 22) | NM_006206 |
| SOX2 | TGCGAGCGCTGCACAT (SEQ ID NO: 23) | GCAGCGTGTACTTATCCTTCTTCA (SEQ ID NO: 24) | NM_003106.2 |
| SOX10 | CCACGAGGTAATGTCCAACATG (SEQ ID NO: 25) | CATTGGGCGGCAGGTACT (SEQ ID NO: 26) | NM_006941.3 |

Neonatal Xenograft into Shiverer Mice. Homozygous shiverer mice (The Jackson Laboratory, Bar Harbor, Me., USA) were crossed with homozygous rag2-null immunodeficient mice (Shinkai et al., "RAG-2-Deficient Mice Lack Mature Lymphocytes Owing to Inability to Initiate V(D)J Rearrangement," *Cell* 68:855-867 (1992), which is hereby incorporated by reference in its entirety) on the C3H background (Taconic, Germantown, N.Y., USA) for generation of shi/shixrag2$^{-/-}$ myelin-deficient, immunodeficient mice. The hiPSC-derived OPCs were prepared for transplantation as described for in vitro coculture. Neonatal pups were either transplanted bilaterally in the corpus callosum with a total of 100,000 cells, as described in Windrem et al., "Fetal and Adult Human Oligodendrocyte Progenitor Cell Isolates Myelinate the Congenitally Dysmyelinated Brain," *Nat. Med.* 10:93-97 (2004), which is hereby incorporated by reference in its entirety, or with 300,000 cells, using the procedure described in Windrem et al., "Neonatal Chimerization With Human Glial Progenitor Cells Can Both Remyelinate and Rescue the Otherwise Lethally Hypomyelinated Shiverer Mouse," *Cell Stem Cell* 2:553-565 (2008), which is hereby incorporated by reference in its entirety. At 3 months of age, transplanted mice were anesthetized with pentobarbital, then perfusion fixed with cold HBSS$^{+/+}$ followed by 4% paraformaldehyde. All procedures were approved by the University Committee on Animal Resources. Brains were extracted and postfixed for 2 hr in cold paraformaldehyde. Brains processed for electron microscopy were perfused in 4% paraformaldehyde and 0.25% glutaraldehyde.

Immunohistochemistry of Tissue Sections. Human cells were identified with mouse anti-hNA, clone 235-1 (MAB1281 at 1:800; Millipore, Billerica, Mass., USA). Phenotypes were identified with human-specific NG2 (MAB2029 at 1:200; Millipore), rat anti-MBP (Ab7349 at 1:25), rabbit anti-OLIG2 (Ab33427 at 1:1000; Abcam, Cambridge, Mass., USA), human-specific mouse anti-GFAP (SMI-21 at 1:500), mouse anti-NF (SMI-311 and SMI-312 at 1:1,000; Covance, Princeton, N.J., USA), and rabbit anti-Ki67 (RM-9106 at 1:200; Thermo-Fisher, Freemont, Calif., USA). Alexa Fluor secondary antibodies, including goat anti-mouse, -rat, and -rabbit antibodies conjugated to 488, 568, 594, and 647 nm fluorophores, were used at 1:400

(Invitrogen, Carlsbad, Calif., USA). PAX6, NKX2.2, OCT4, NANOG, and SOX2 antibodies were employed using the same conditions as in vitro.

Myelinated Axon Counts. Regions of dense engraftment with human cells were selected for NF and MBP staining; a 1 µm stack of ten superimposed optical slices taken at 0.1 µm intervals (Olympus FluoView 300) was made for each of three fields of view in the corpus callosum. Three parallel, equidistant lines were laid over the images perpendicular to the axons. Axons were scored at intersections with the lines as either myelinated (closely apposed to MBP on both sides) or unmyelinated.

Mapping of Human Cell Engraftment. The positions of all anti-human nuclei+ cells were mapped on 20 µm coronal sections at 160 µm intervals from −3.2 to 1.2 bregma anterior-posterior.

Cell Counting. Three unilateral, equally spaced samples of corpus callosum, from −0.4 to 1.2 bregma, were counted for cells expressing hNA together with either MBP, hGFAP, OLIG2, or Ki67. White matter was also assessed for the presence of any hNA+ cells coexpressing HuC/HuD, OCT4, or NANOG. All data are provided as means±SEM.

Electron Microscopy. Samples of human iPSC-derived glial chimeric white matter were taken from mice killed at 22-40 weeks of age, perfused with half-strength Karnovsky's fixative, then processed for ultrastructural analysis of myelin morphology and quality using previously described techniques (Windrem et al., "Neonatal Chimerization With Human Glial Progenitor Cells Can Both Remyelinate and Rescue the Otherwise Lethally Hypomyelinated Shiverer Mouse," *Cell Stem Cell* 2:553-565 (2008), which is hereby incorporated by reference in its entirety).

Figure 2:
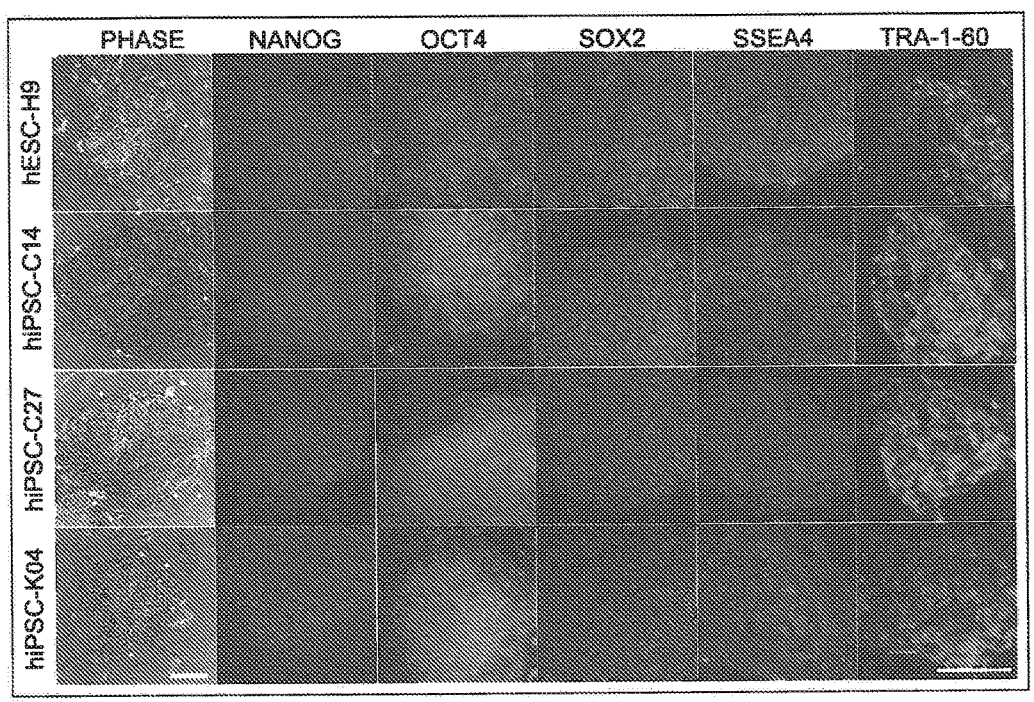
FIG. 2 shows the characterization of hiPSC lines. All three hiPSC lines in this study show hESC-like morphology (phase images), when compared to the hESC line WA09/H9 (top row). Immunolabeling confirmed that the hiPSCs expressed NANOG, OCT4, SOX2, SSEA4 and TRA-1-60 immunoreactivities. Scale: 200 μm.

Cell Preparation. Stage 1 Both hESCs and hiPSCs were cultured on irradiated mouse embryonic fibroblast (MEF) cells, and fed daily with hESC medium, consisting of DMEM/F12 containing with 20% KO-serum replacement, supplemented with bFGF (4 ng/ml, Invitrogen). Both hESC and hiPSCs were passaged when they reached 80% confluence in colonies of 250-300 µm diameter, typically every 3-4 days for WA09/H9 and every 4 (K04 cells) or 7 days (C14 and C27) for hiPSCs. The undifferentiated stem cells were validated immunocytochemically for their expression of human pluripotent stem cell markers, that included SSEA4, TRA-1-60, OCT4, NANOG, and SOX2 (FIG. 2). Of note, both OCT4 and SOX2 were also utilized as reprogramming factors in the generation of the hiPSCs, the generation of which have been previously described. Cells were passaged by incubation in collagenase type IV (1 mg/ml, Invitrogen) for 5-10 min, followed by gentle scraping from the culture dish, after which they were triturated 5 times through a polished glass pipette and then spun, washed and resuspended twice. The cells were then split 1:3-1:4 onto 6-well plates pre-coated with irradiated MEF cells.

Stage 2 To generate embryonic bodies (EB), hESC or hiPSC cultures were dissociated using Dispase (0.5 mg/ml, Invitrogen) at 37° C. for 5-10 min, once they achieved 80% confluence with colony diameters of 250-300 m, in the absence of evident differentiation. These criteria proved important, as it was noted that the quality of hESC and hiPSC cultures at the stage 1-2 transition critically affected that of their derived EBs, as well as their subsequent differentiation into OPCs. The EBs were cultured in suspension in tissue culture flasks (Nunc EasYFlasks, Thermo Scientific) in ESC medium without bFGF for 5 days; then switched to neural induction medium (NIM; DMEM/F12 supplemented with non-essential amino acids and N2) supplemented with bFGF (20 ng/ml, Sigma) and heparin (2 µg/ml, Sigma), for either 2 days (WA9/H9 hES) or 7 days (K04, C14 and C27 hiPSCs). Thereafter, the EBs were plated onto laminin/poly-ornithine coated 6-well plates and cultured in NIM supplemented with bFGF, heparin and laminin (10 µg/ml) for 3 additional days; the medium was then switched to NIM supplemented with retinoic acid (RA, 100 nM, Sigma), for 4 days.

Figures 3A, 3B, 3C, 3D, 3E, 3F, 3G, 3H, 3I, 3J:
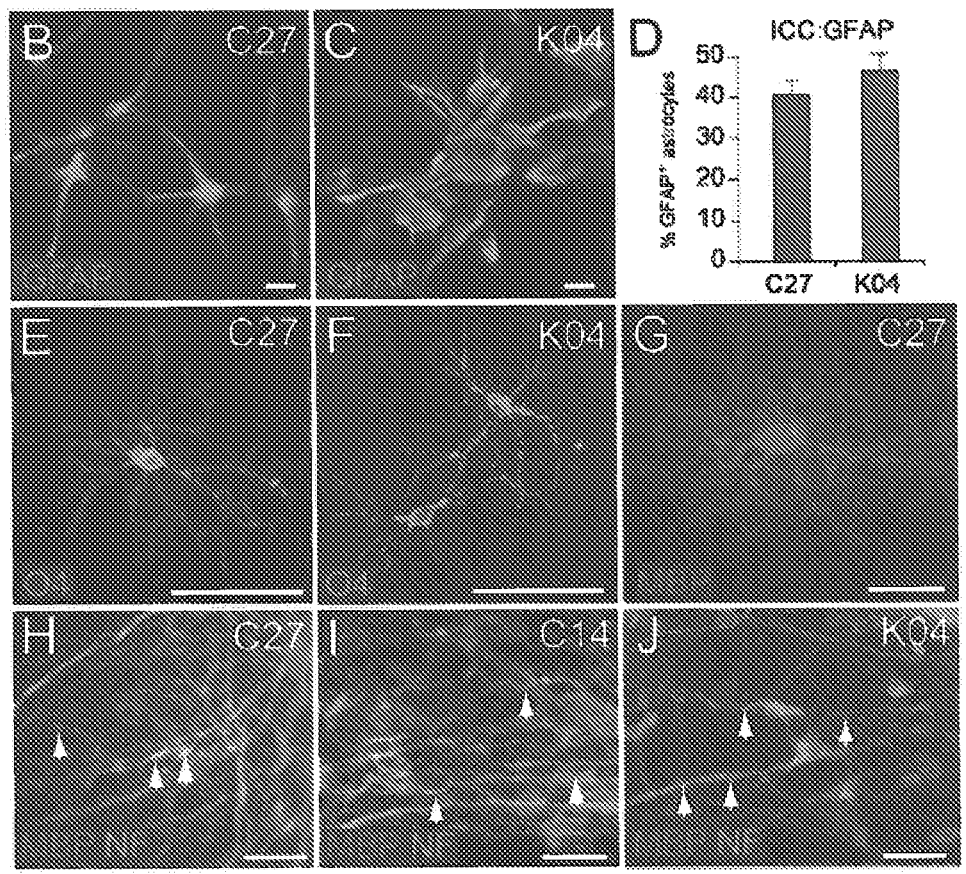
FIGS. 3A-3J demonstrate that both astrocytes and oligodendroctyes are efficiently generated from hiPSC OPCs.
Figures 4A, 4B, 4C, 4D, 4E, 4F, 4G, 4H, 4I:
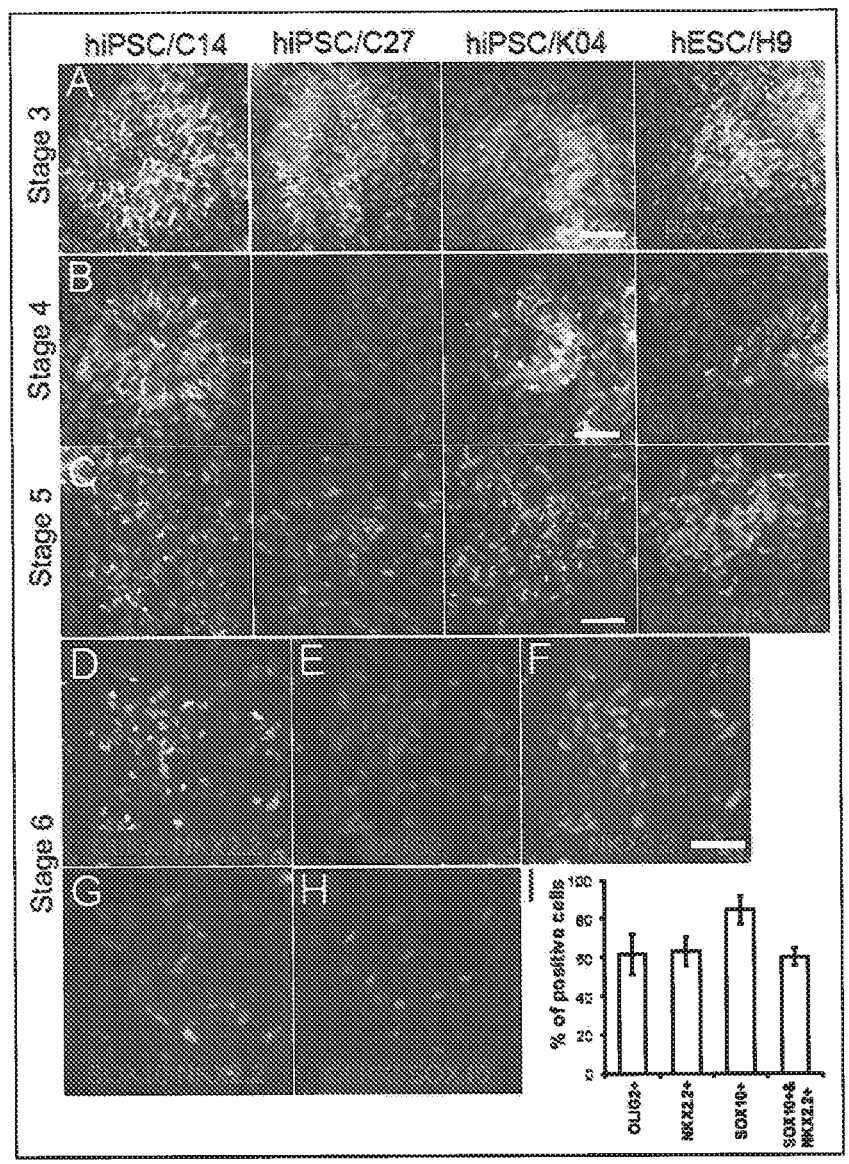
FIGS. 4A-4M show serial neuroepithelial and glial differentiation from hiPSCs.

Stage 3 The neuroepithelial differentiation efficiency at this point, the end of stage 3, was assessed by immunolabeling for PAX6 and SOX1; co-expression of these markers characterizes central neural stem and progenitor cells. The yields of neuroepithelial colonies, defined as (PAX6+/SOX1+)/total rosette-like colonies, were 52.2±7.5%, 78.4±4.7%, and 76.0±7.0% from K04, C14 and C27 cultures, respectively (N=3-6 scored cultures/line). The efficiencies of neuroepithelial colony production from C14 and C27 hiPSCs were similar to those for WA09/H9 (75.4±8.8%) (FIGS. 3A and 4A).

Stage 4 On day 14 (for H9) or day 19 (for K04 and C27) (end of stage 3, 4 days after addition of RA), purmorphamine (1 µM, Calbiochem), a sonic hedgehog (shh) agonist, and B27 (Invitrogen) were added to the media. The cultured NE colonies were detached mechanically 9 days later, at either 23 DIV (WA9/H9 hES) or 28 DIV (K04, C14 and C27 hiPSC), and then cultured in suspension in 6-well Ultralow cluster plates (FIG. 4B).

Stage 5 One day after plating into Ultralow cluster plates, the medium was replaced with NIM supplemented with bFGF (10 ng/ml), in addition to purmophamine and B27. At that point the phenotypic composition of aliquots was assessed by staining of OLIG2 and/or NKX2.2, to ascertain the appearance of pre-OPC colonies following RA treatment. Both OLIG2 and NKX2.2 are expressed by central OPCs, though NKX2.2 is the more specific indicator of oligodendroglial differentiation (see citations 16-17). At this early pre-OPC stage, the percentage of OLIG2-expressing colonies was higher than that of NKX2.2+ colonies, reflecting the earlier appearance of OLIG2 (FIGS. 3A and 4C). In contrast, by the end of stage 5 (35 DIV for WA09/H9 or 40 DIV for K04, C14 and C27), under the effect of bFGF without RA, more NKX2.2+ colonies appeared, concurrent with the peak of OLIG2 expression. By the end of this stage, the percentage of OLIG2+/NKX2.2+ co-expressing colonies was similar among all four lines in this study (FIG. 3A).

Stage 6 To initiate stage 6 (day 35 for WA09/H9 or day 40 for K04, C14 and C27), the OLIG2/NKX2.2-defined pre-OPCs in stage 5 suspension culture were switched to glial induction media (GIM; DMEM/F12, N1, B27, T3 at 60 ng/ml, biotin at 100 ng/ml, dibutyryl-cAMP at 1 µM; all from Sigma) supplemented with PDGF AA (10 ng/ml), IGF-1 (10 ng/ml), and NT3 (10 ng/ml). During this long period of OPC suspension culture, ⅔ of the media volume was changed every 3 days. The resultant stage 6 gliospheres were prevented from aggregating by gentle trituration through P1000 pipette tips during media changes.

Beginning at 95 DIV, the efficiency of hOPC differentiation, as defined by A2B5, CD140a and CD140a/CD9 co-expression, was assessed both in vitro and in vivo, using ICC, qRT-PCR, and xenograft into neonatal shiverer mice at serial time points. Gliospheres were capable of yielding both mature oligodendrocytes and myelinogenic OPCs as of 120 DIV. Between 120-200 DIV, the incidence of OPC-bearing colonies rose steadily, such that the proportion of OLIG2 and NKX2.2 co-expressing colonies of OPCs from K04, C14 and C27 were 73.8±8.7%, 78.9±6.1% and 79.5±8.5%, respectively. Interestingly, the efficiency of hOPC production by hiPSC cells was consistently higher than that exhibited by WA09/H9 cells (45.4±20.3%) (FIG. 3A).

Figures 11A, 11B, 11C, 11D, 11E:
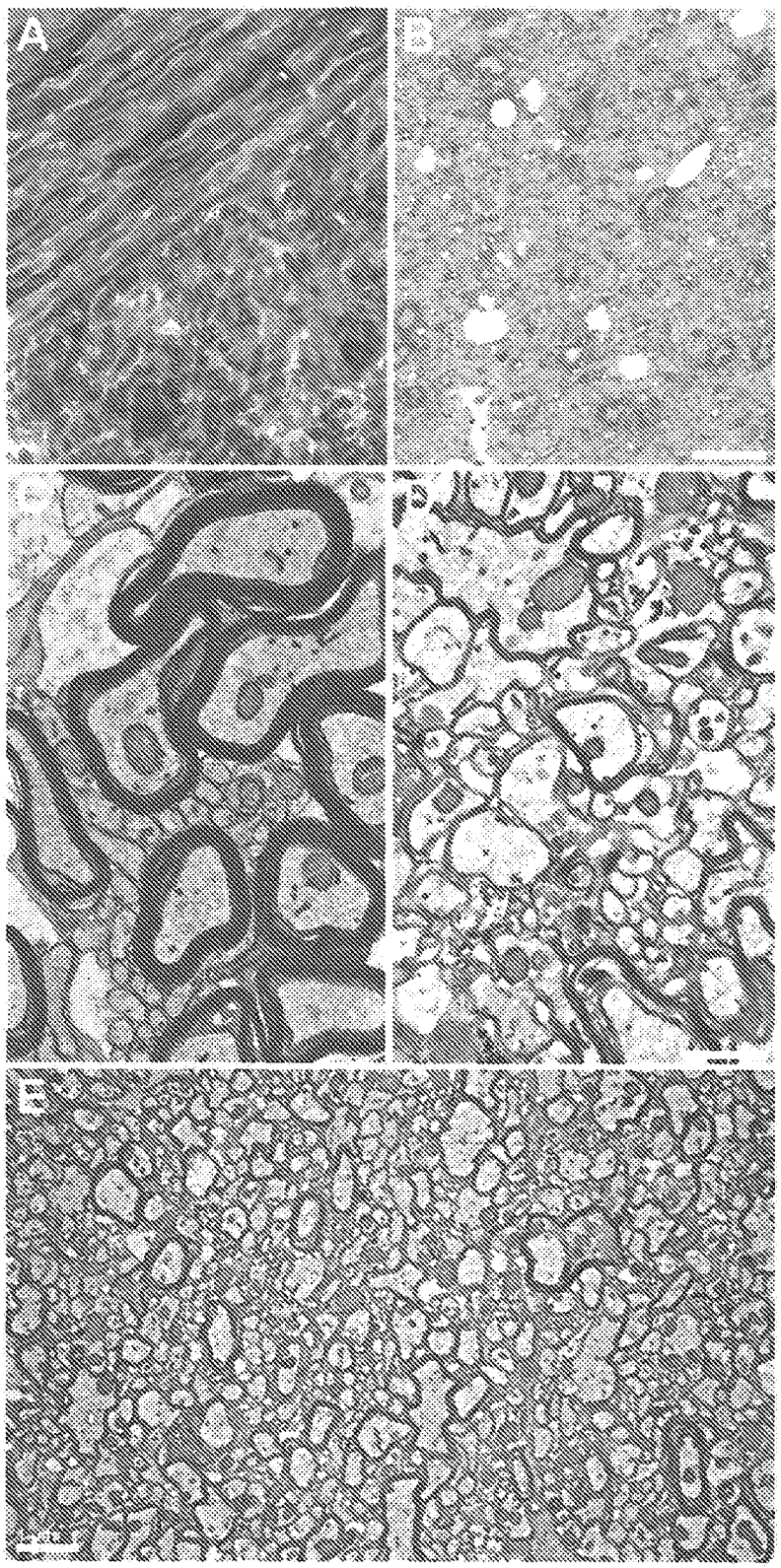
FIGS. 11A-11E show myelination in hiPSC-OPC-transplanted but not in untreated Shiverer mice. Toluidine blue stained semi-thin sections through the corpus callosum and cortical layer VI in C27 hiPSC-derived OPC-transplanted (FIG. 11A) or untreated (FIG. 11B) shiverer brain.

Late Stage 6/Pre-Transplant By this point (late stage 6), the newly produced hOPCs also expressed other OPC markers, such as CD140a/PDGFRα and SOX10, which typically co-expressed OLG2 or NKX2.2 (FIGS. 4D-4H). At this stage the percentages of the OLG2+, NXK2.2+ or SOX10+, among all DAPI-identified cells, were 61.9±10.3%, 63.4±7.3%, and 84.6±7.0% among hiPCS/K04-derived OPCs, while the corresponding proportion of NKX2.2/SOX10 co-expressing OPCs was 60.6±4.4% (FIG. 4I). To further validate the efficiency of OPC differentiation, RT-PCR for OLIG2, NKX2.2 and GFAP mRNA was performed, and all genes were substantially upregulated in stage 6 OPCs, as were their corresponding protein products (FIGS. 11C-D and 3C).

Flow Cytometric Protocols and Analysis. Flow cytometry of hESC- or hiPSC-derived OPCs was performed on a FACSAria IIIU (Becton Dickinson, San Jose, Calif.). Cells were gently scraped from the culture dishes and then treated with Accutase (Chemicon) at 37° C. for 5 minutes with gentle shaking. The samples were then triturated with a narrow glass Pasteur pipette until a single cell suspension was obtained. The cells were then spun and resuspended in Miltenyi Washing Buffer (MWB) at $1 \times 10^6$ cells/ml. The primary antibodies, directly conjugated antibodies or their corresponding isotype controls were added to the cells at the concentrations listed below, then incubated on ice for 15 minutes. 5 ml of MWB was added and the cells were spun down. For the non-conjugated antibodies, the pelleted cells were resuspended in MWB to $1 \times 10^6$ cells/ml and the appropriate secondary antibody, Alexa-488 conjugated goat anti-mouse IgM, was added at 1:500 dilution. The samples were incubated on ice for 15 minutes and then washed with 5 ml of MWB for 10 minutes. All samples were then resuspended in Phenol Red-free DMEM/F-12 to a concentration of $1\text{-}1.5 \times 10^6$ cells/ml, then passed through a 40-μm cell strainer (Becton Dickinson, BD). DAPI was added at 1 g/ml; the cells were analyzed by forward and side scatter, for PE fluorescence through a 582±15 nm band-pass filter, for Alexa Fluor 488/FITC fluorescence through a 530±30 nm band-pass, for PERCP-Cy5.5 through a 695±40 nm band-pass, and for DAPI fluorescence through a 450±50 nm band-pass. Unstained cells were used to set the background fluorescence; a false positive rate of 0.5% was accepted. The antibodies used were mouse IgM isotype control (Chemicon, PP50), mouse anti-A2B5 (IgM, Chemicon, MAB312), mouse anti-O4 (IgM, Chemicon, MAB345), PE mouse $IgG_{2a}$, κ isotype control (BD, 555574), PE mouse anti-human CD140a ($IgG_{2a}$, BD, 556002), PERCP-Cy5.5 mouse $IgG_1$ isotype control (BD, 347212) and PERCP-Cy5.5 mouse anti-human CD9 ($IgG_1$, BD, 341649).

In Vitro Immunocytochemistry. Pluripotent hESC or hiPSCs raised on irradiated MEF cells were cultured for 3 to 4 days prior to fixation with 4% paraformaldehyde. Similarly, the differentiated neurogenic or gliogenic clusters were plated onto poly-ornithine and laminin coated 24-well plate and cultured for 3 days before being fixed with 4% paraformaldehyde. The gliogenic spheres containing hOPCs at later stages were dissected into small fragments and plated onto poly-ornithine/laminin coated 24-well plates, and cultured for 2-4 weeks before being fixed, depending on the experiment. Fixation was performed with 4% paraformaldehyde for 5 min at room temperature followed by 3 washes with PBS. Immunolabeled cells were incubated with primary antibodies overnight at 4° C. and with secondary antibodies for 0.5 h at 25° C. Primary antibodies included: mouse anti-OCT4, mouse anti-SSEA4, mouse anti-TRA-60 (all were used in 1:100 dilution and were from Chemicon); rabbit anti-NANOG (1:500, Abcam); rabbit anti-PAX6 (1:400, Covance); goat anti-OLIG2 (1:200, R&D); mouse anti-NKX2.2 (1:100, DSHB); rabbit anti-PDGFR (1:400, Santa Cruz Biotechnology); rabbit anti-SOX10 (1:400, Advanced Bioscience Resources); goat anti-SOX1 (1:100, R&D Systems); goat anti-SOX2 (1:1000, R&D Systems mouse anti-GFAP (1:400, Covance); rabbit anti-GFAP (1:1000, Chemicon); NESTIN (1:1000, Millipore Bioscience Research Reagents); mouse anti-III-tubulin (1:1000, Covance); oligodendrocytic sulfatide, as recognized by MAb O4 (1:100, Millipore Bioscience); and rat anti-MBP (1:25, Abcam).

Example 1

Human iPSCs can be Efficiently Directed to Glial Progenitor Cell Fate

Four different iPSC lines from three different sources were used for this study; these included WA09/H9 hESCs (Thomson et al., "Embryonic Stem Cell Lines Derived From Human Blastocysts," *Science* 282:1145-1147 (1998), which is hereby incorporated by reference in its entirety); keratinocyte-derived K04 hiPSCs (Maherali et al., "A High-Efficiency System for the Generation and Study of Human Induced Pluripotent Stem Cells," *Cell Stem Cell* 3:340-345 (2008), which is hereby incorporated by reference in its entirety); and fibroblast-derived C14 and C27 hiPSCs (Chambers et al., "Highly Efficient Neural Conversion of Human ES and iPS Cells by Dual Inhibition of SMAD Signaling," *Nat. Biotechnol.* 27:275-280 (2009), which is hereby incorporated by reference in its entirety). Specific features of several published protocols were selected for the production of glial progenitor cells from hESCs (Hu et al., "Differentiation of Human Oligodendrocytes From Pluripotent Stem Cells," *Nat. Protoc.* 4:1614-1622 (2009); Izrael et al., "Human Oligodendrocytes Derived From Embryonic Stem Cells: Effect of Noggin on Phenotypic Differentiation in Vitro and on Myelination in Vivo," *Mol. Cell. Neurosci.* 34:310-323 (2007), which are hereby incorporated by reference in their entirety) and then optimized to produce the resultant hybrid protocol for use with WA09/H9 hESCs. The resultant protocol was modified to further optimize its efficiency with the three hiPSC lines, which were derived in different labs, from different cell sources, and using different reprogramming protocols (Chambers et al., "Highly Efficient Neural Conversion of Human ES and iPS Cells by Dual Inhibition of SMAD Signaling," *Nat. Biotechnol.* 27:275-280 (2009); Maherali et al., "A High-Efficiency System for the Generation and Study of Human Induced Pluripotent Stem Cells," *Cell Stem Cell* 3:340-345 (2008), which are hereby incorporated by reference in their entirety) (FIG. 2). The resultant six-stage OPC differentiation protocol, which spans a range of 110-150 days in vitro as described above and schematized in FIG. 1, efficiently generated human OPCs (hOPCs) as well as their mature progeny, including both astrocytes and OLs, from hESCs and hiPSCs alike (FIGS. 1B-1P). Its efficiency of OPC production, as defined by the incidence of OLIG2+/NKX2.2+ gliogenic (Qi et al., "Control of Oligodendrocyte Differentiation by the Nkx2.2 Homeodomain Transcription Factor," *Development* 128:2723-2733 (2001); Zhou et al., "The bHLH Transcription Factor Olig2 Promotes Oligodendrocyte Differentiation in Collaboration with Nkx2.2," *Neuron* 31:791-807 (2001); Zhou et al., "Identification of a Novel Family of Oligodendrocyte Lineage-Specific Basic Helix-Loop-Helix Transcription Factors," *Neuron* 25:331-343 (2000), which are hereby incorporated by reference in their entirety) cell clusters in stage 6, ranged from 45.4±20.3% in WA09/H9-derived hESCs to 73.8±8.7%, 78.9±6.1%, and 79.5±8.5% in K04-, C14-, and C27-derived OPCs, respectively (all data are provided as means±SEM; FIGS. 3A and 4). Thus, each of the hiPSC and hESC lines could be directed into highly enriched preparations of OLIG2+/PDGFRa+/NKX2.2+/SOX10+ OPCs. Indeed, the efficiencies of OPCs' differentiation from hiPSCs, whether induced from keratinocytes (K04 cells) or fibroblasts (C14 and C27 cells), were consistently higher than that of WA09/H9 hESCs.

Example 2

Both Astrocytes and OLs are Efficiently Derived from hiPSC-Derived hOPCs

Both in vitro and in vivo, hiPSC OPCs readily differentiated into astrocytes as well as OLs. GFAP-defined astroglia first appeared by 70 days in vitro (DIV), significantly earlier than OLs did. By late stage 6, at 120 DIV, GFAP+ astrocytes were found to be abundant when gliogenic spheres were plated onto a polyornithine/laminin-coated surface (FIGS. 3B-3D). By that time, GFAP+ cells comprised 40%-50% of cells in OPC-induced cultures, across all cell lines (FIG. 3D). Quantitative RT-PCR confirmed the upregulation of GFAP messenger RNA (mRNA) expression during OPC differentiation in all cell lines (Table 2).

TABLE 2

Astrocytic appearance during OPC induction: qPCR of GFAP

| hiPSC lines | Stage 1 | n | Stage 6 | n |
|---|---|---|---|---|
| C27 | 1.0 ± 0.1% | 4 | 15,801.8 ± 7393.7% | 4 |
| K04 | 1.0 ± 0.1% | 3 | 9,623.6 ± 2434.6% | 5 |
| WA09/H9 | 1.0 ± 0.1% | 5 | 5,077.1 ± 3526.9% | 3 |
| % ± SEM | | | | |

Human iPSC cultures were subjected to quantitative real-time PCR (qPCR) for astrocytic glial fibrillary acidic protein (GFAP) (normalized to GAPDH), as a dual function of cell line and stage of OPC differentiation in vitro. All data are provided as means ± SEM.

The production of OLs from hESC and hiPSC-derived OPCs was triggered by the withdrawal of gliogenic growth factors to half-normal levels (see Materials and Methods). When hiPSC OPCs were exposed to those conditions for 2 weeks, a proportion matured into O4+ and/or myelin basic protein (MBP)+ OLs (FIGS. 3E-3G). According to flow cytometry, O4+OLs in C27, C14, and K04 hiPSC-derived OPC cultures respectively comprised 11.9±3.8%, 4.1±0.9%, and 7.6±1.5% of all cells (at 194±15, 186±14, and 205±14 DIV, respectively; means±SEM) (FIG. 5A; Table 3). Of note, the culture conditions favored initial oligodendrocytic differentiation, but not postmitotic oligodendrocytic survival, because the focus was on preparing populations of transplantable lineage-biased progenitors and immature oligodendroglia rather than more mature—but less transplantable—process-bearing OLs.

TABLE 3

Flow cytometric delineation of hiPSC oligodendroglial abundance in vitro

| hiPSC lines | O4+ | Average DIV |
|---|---|---|
| C27 | 11.9 ± 3.8% | 194.3 ± 15 |
| C14 | 4.1 ± 0.9% | 186.0 ± 13.6 |
| K04 | 7.6 ± 1.5% | 204.9 ± 14.0 |
| n = 4-7 | % ± SEM | |

Human iPSC-derived OPCs and early oligodendroglia from different cell lines (C27, C14 and K04) were collected and stained for oligodendrocytic sulfatide, as recognized by MAb O4, late in at stage 6 (>120 days in vitro, DIV), then analyzed by flow cytometry. Results are given as proportions (mean percentages ± SEM) of $O4_+$ cells; N = 4-7 repeats/cell line.

Example 3

Figures 5A, 5B, 5C:
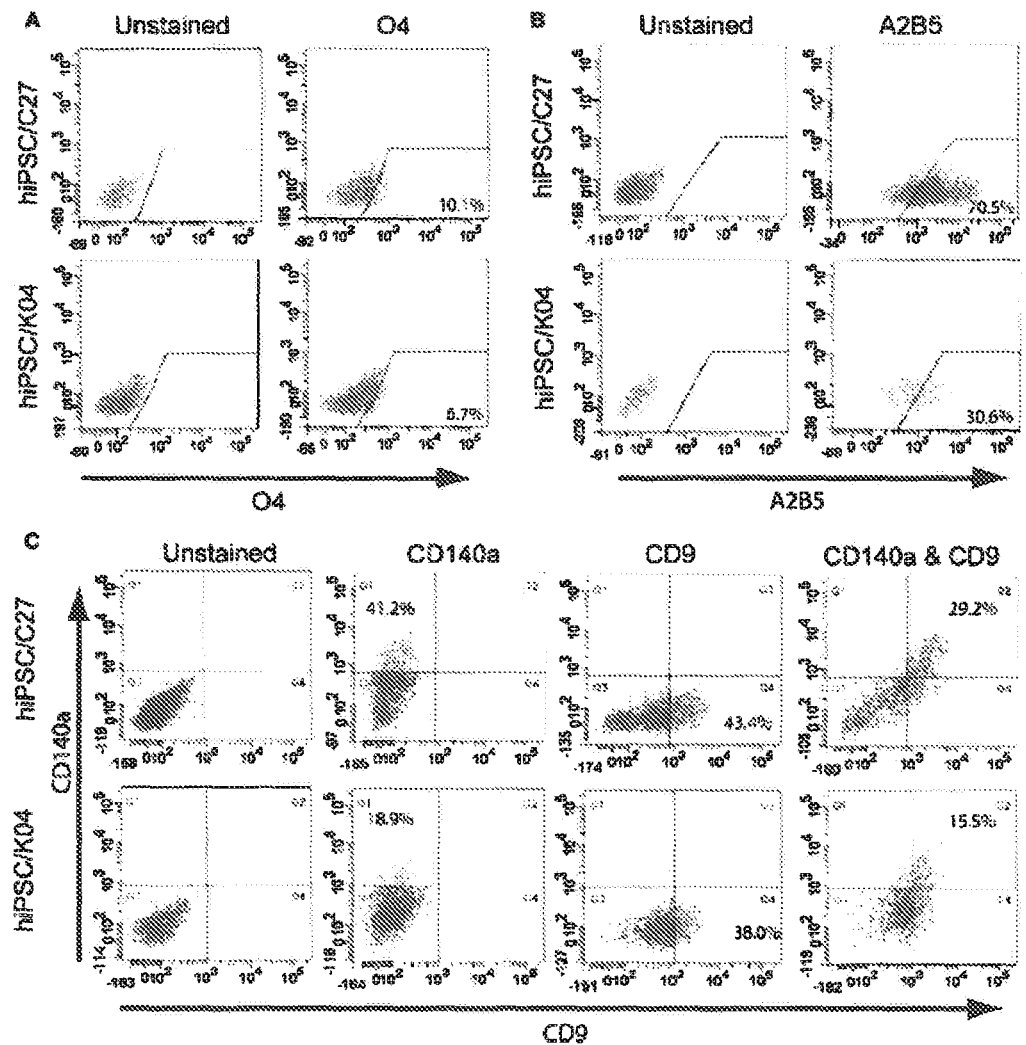
FIGS. 5A-5C show that OPCs can be isolated from mixed hiPSC culture by CD140a- and CD9-Directed FACS.

OPCs could be Isolated from hiPSC Cultures by CD140a- and CD9-Directed Fluorescence-Activated Cell Sorting Flow cytometry for A2B5, CD140a/PDGFaR, and the tetraspanin CD9 (Berry et al., "Cytology and Lineage of NG2-Positive Glia," *J. Neurocytol.* 31:457-467 (2002); Terada et al., "The Tetraspanin Protein, CD9, Is Expressed by Progenitor Cells Committed to Oligodendrogenesis and Is Linked to Beta1 Integrin, CD81, and Tspan-2," *Glia* 40:350-359 (2002), which are hereby incorporated by reference in their entirety) was next used for identifying and quantifying hiPSC OPCs in stage 6 culture (FIGS. 5B and 5C). CD140a+ OPCs derived from C27, C14, and K04 hiPSCs respectively comprised 33.0±10.3%, 32.8±12.0%, and 41.1±6.1% of all cells, compared to 37.5±10.2% of H9-derived cells (FIG. 5C; Table 4). The CD9+ fraction of CD140a+ cells, which defined a later-stage pool of OPCs, comprised 24.0±8.0% and 12.4±2.3% of cells in stage 6 C27 and K04 hiPSC cultures, respectively; matched cultures of H9-derived OPCs included 15.0±4.9% CD9+/CD140a+ cells (FIG. 5C; Table 4; n=4-7 repeats each). Thus, hiPSC OPCs could be identified and isolated at different stages of lineage restriction, which were serially represented by A2B5, CD140a, CD9, and O4. Selection based on these epitopes permits the isolation of relatively pure populations of hiPSC OPCs while removing residual undifferentiated cells from the isolate.

TABLE 4

Flow cytometry of cell-selective surface markers during OPC induction

| hiPSC lines | CD140a+ | CD9+ | CD140a+/CD9+ | A2B5+ | Average DIV |
|---|---|---|---|---|---|
| C27 | 33.0 ± 10.3% | 40.5 ± 5.6% | 24.0 ± 8.0% | 67.1 ± 12.5% | 168.7 ± 14 |
| C14 | 32.8 ± 12.0% | 28.5 ± 5.3% | 16.2 ± 7.0% | 31.5 ± 20.3% | 165.8 ± 11 |
| K04 | 41.1 ± 6.1% | 19.3 ± 3.6% | 12.4 ± 2.3% | 25.6 ± 4.5% | 177.2 ± 12.7 |
| W09/H9 | 37.5 ± 10.2% | 22.3 ± 5.3% | 15.0 ± 4.9% | 15.0 ± 4.9% | 148.2 ± 19.5 |
| n = 4-7 | % ± SEM | | | | |

The OPCs derived from 3 different hiPSC cell lines (C27, C14 and K04), as well as from hESCs (WA9/H9), were collected and stained for CD140a, CD9, or A2B5 late in stage 6 (>120 DIV), then analyzed by flow cytometry. Data include the average proportion (mean ± SEM) of $CD140a_+$, $CD9_+$, $CD140a_+/CD9_+$ and $A2B5_+$ cells (n = 4 to 7 repeats/cell; mean ± SEM).

Example 4 hiPSC-Derived OLs Generate MBP in Contact with Human Axons In Vitro

The ability of hiPSC OLs to myelinate axons in vitro was examined. hiPSC OPCs from each cell line were cocultured gestational age (g.a.) fetal brain using polysialyted neural cell adhesion molecule (PSA-NCAM)-directed selection (Windrem et al., "Neonatal Chimerization With Human Glial Progenitor Cells Can Both Remyelinate and Rescue the Otherwise Lethally Hypomyelinated Shiverer Mouse," *Cell Stem Cell* 2:553-565 (2008), which is hereby incorporated by reference in its entirety). The neurons were cultured on laminin for 10-14 days to allow phenotypic maturation and fiber extension and were confirmed to be free of tissue-derived OLs by O4 immunolabeling. hiPSC OPCs were then prepared as clusters of 50-100 mm in diameter and cocultured with the fetal neurons for 4 weeks; the cultures were then immunolabeled for MBP and neurofilament (NF). Confocal imaging revealed abundant MBP+ processes that contacted axons and initiated ensheathment (FIGS. 3H-3J), though unambiguous myelin formation was not noted at the time points imaged. Thus, to better assess myelinogenesis by hiPSC OPCs, their engraftment and myelination in vivo was evaluated.

Example 5 hiPSC OPCs Efficiently and Functionally Myelinate the Shiverer Brain

Figures 6A, 6B, 6C, 6D, 6E, 6F, 6G:
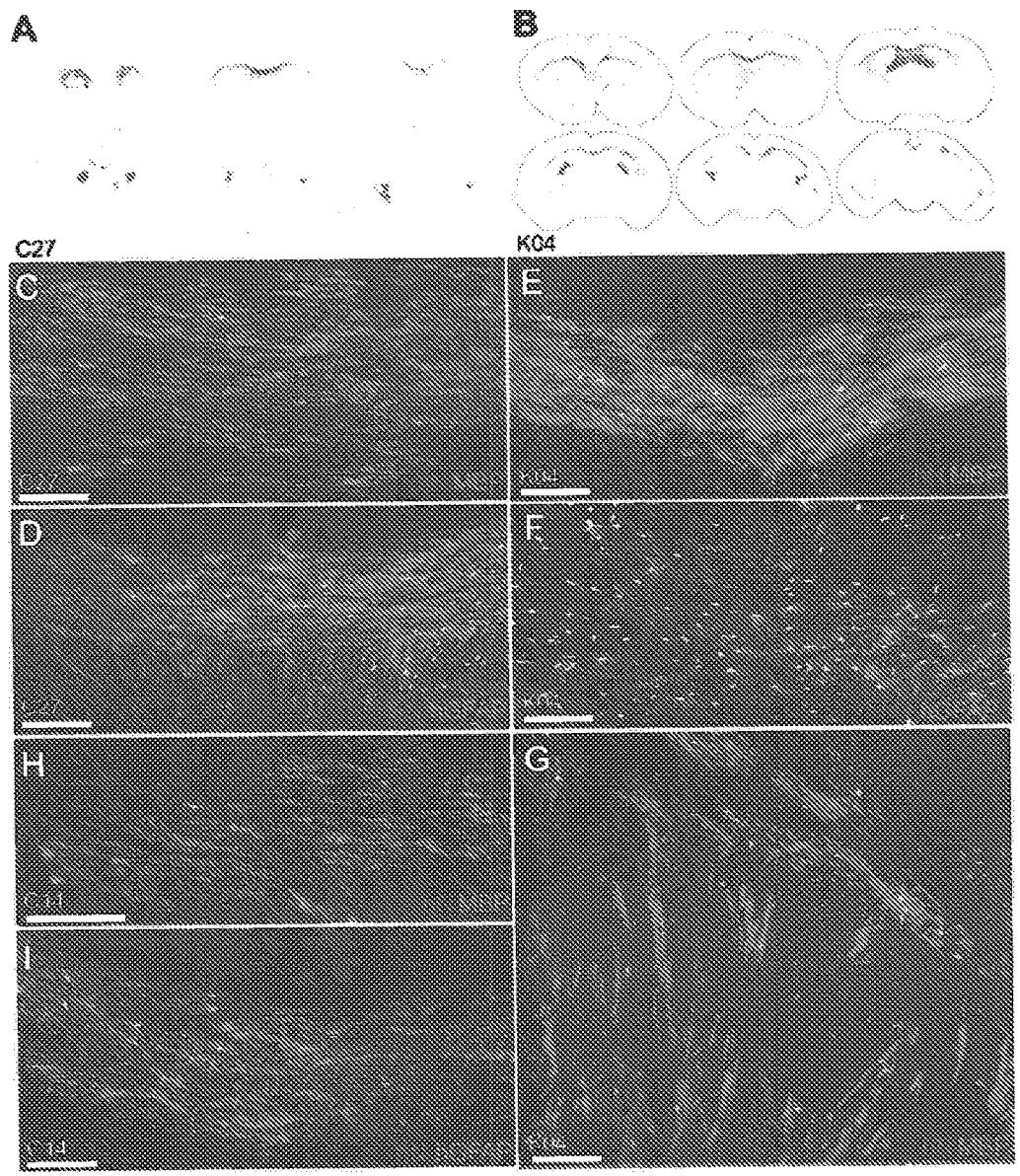
FIGS. 6A-6G demonstrate that hiPSCs migrate widely and differentiate as astroglia and myelinogenic OLs. hiPSC OPCs generated from all three hiPSC lines migrated throughout the shiverer brain, engrafting most densely in white matter. Distributions of C27 (FIG. 6A) and K04 (FIG. 6B) hiPSC-derived OPCs are shown (hNA$^+$, red, mapped in Stereo Investigator). By 13 weeks of age, C27 hiPSC OPCs (FIG. 6C), K04 hiPSC OPCs (FIGS. 6E and 6G), and C14 hiPSC OPCs (FIG. 6H) matured into MBP-expressing oligodendroglia (green) throughout the subcortical white matter, including callosal and capsular (FIGS. 6C, 6E, and 6H) as well as striatal (FIG. 6G) tracts. In these 13-week-old shiverer mouse recipients, C27 (FIG. 6D), K04 (FIG. 6F), and C14 (FIG. 6I) hiPSC-derived OPCs also differentiated as astroglia (human-specific GFAP, green), especially as fibrous astrocytes in the central white matter. Scale: 100 μm (FIG. 6C-6I).

To definitively establish the myelination competence of hiPSC OPCs, these cells were transplanted into newborn homozygous shiverer (shi/shi)×rag2$^{-/-}$ immunodeficient mice. For this experiment, the mice were implanted with 100,000 hiPSC-derived OPCs bilaterally into the corpus callosum (n=4-7 mice per hiPSC line for K04, C27, and C14 hiPSC-derived OPCs), using previously described methods (Windrem et al., "Neonatal Chimerization With Human Glial Progenitor Cells Can Both Remyelinate and Rescue the Otherwise Lethally Hypomyelinated Shiverer Mouse," *Cell Stem Cell* 2:553-565 (2008), which is hereby incorporated by reference in its entirety). At 3 or 4.5 months of age, the mice were killed and their brains were analyzed in terms of donor cell distribution and density, myelin production and the proportion of myelinated axons, and nodal reconstitution. All three of the hiPSC line-derived OPCs were able to robustly myelinate the recipient brains; from each line, high donor cell densities and widespread dispersal were observed throughout the forebrain white matter (FIGS. 6A and 6B). C27, C14, and K04 hiPSC OPC-derived oligodendrocytic differentiation and myelination were analogous in extent, with robust myelination of the corpus callosum and capsules (FIGS. 6C, 6E, 6H, 7B, 7G, and 7J). As a result of the superior initial neutralization of these two lines relative to C14, higher net yields of OPCs were achieved with C27 and K04 hiPSCs and hence quantitative assessment of myelination in recipients of C27 or K04 hiPSC OPCs was pursued.

Figures 7A, 7B, 7C, 7D, 7E, 7F, 7G, 7H, 7I, 7J, 7K:
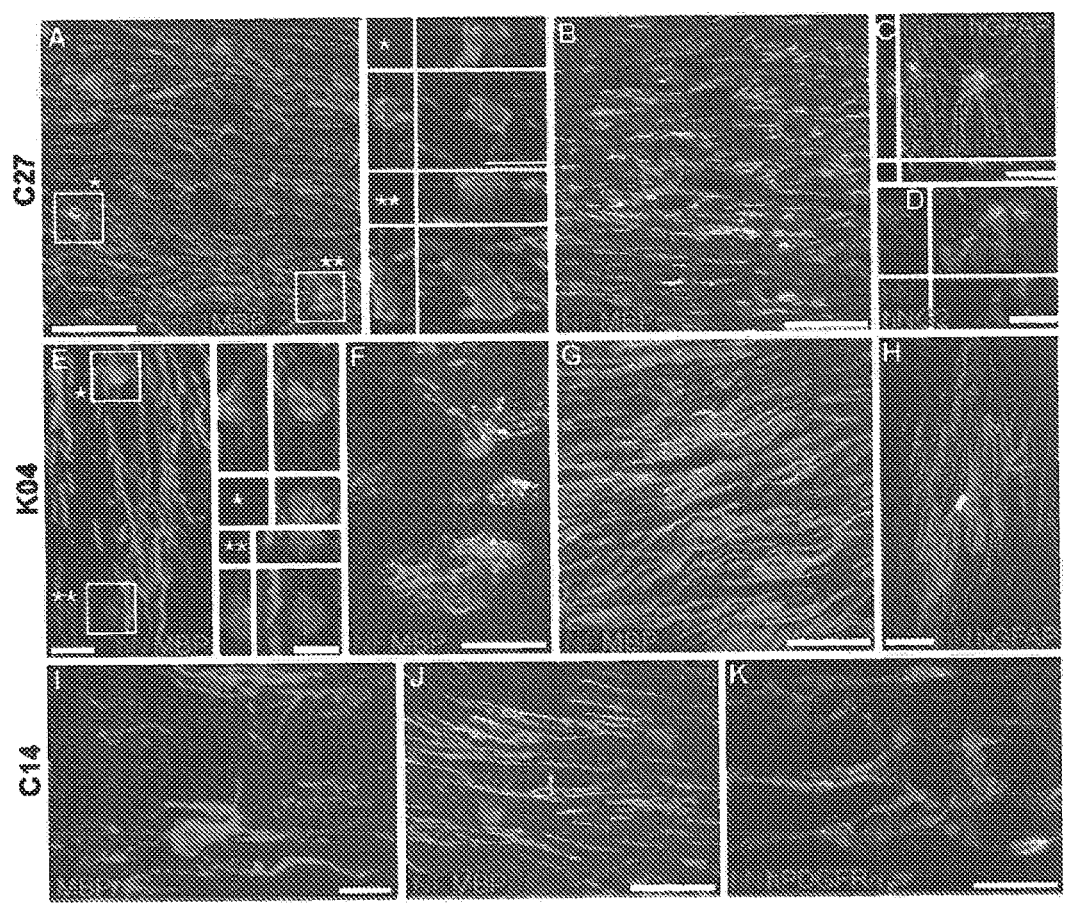
FIGS. 7A-7K show that hiPSC OPCs robustly myelinate in vivo. Confocal images of the callosal and capsular white matter of mice engrafted with hiPSC OPCs derived from all three tested hiPSC lines demonstrate dense donor-derived myelination: C27-derived (FIGS. 7A and 7B), K04-derived (FIGS. 7E-7G), and C14-derived (FIGS. 7I and 7J).

Quantitative histology revealed that within the corpus callosa of 3 month (13 week)-old shiverer recipients, C27 and K04 hiPSC-derived OPCs and oligodendroglia, defined as human nuclear antigen (hNA)+/OLIG2+, achieved densities of 29,498±13,144 and 37,032±8,392 cells/mm³, respectively. Among these, 7,298±2,659 (C27) and 2,328±650 (K04) cells/mm³ expressed MBP; these comprised 10.9±5.1% (C27) and 4.7±1.1% (K04) of all donor cells within the sampled midline of the corpus callosum at the 13 week time point. To assess the myelination efficiency in terms of the proportion of axons myelinated, confocal analysis was used to quantify the fraction of callosal axons ensheathed by hiPSC oligodendroglia in the three mice engrafted with C27 hiPSC-derived OPCs. At the 13 week time point analyzed, 17.2±7.2% of host mouse axons were ensheathed within the three sampled callosa (FIG. 7B). Remarkably, the density of hiPSC-OPC donor derived myelination and the proportion of ensheathed axons at 13 weeks proved as high as, and exceeded, those achieved by OPCs derived from second-trimester fetal brain tissue, whether isolated as A2B5+/PSA-NCAM− or CD140a+ cells (Sim et al., "CD140a Identifies a Population of Highly Myelinogenic, Migration-Competent and Efficiently Engrafting Human Oligodendrocyte Progenitor Cells," *Nat. Biotechnol.* 29:934-941 (2011); Windrem et al., "Fetal and Adult Human Oligodendrocyte Progenitor Cell Isolates Myelinate the Congenitally Dysmyelinated Brain," *Nat. Med.* 10:93-97 (2004); Windrem et al., "Neonatal Chimerization With Human Glial Progenitor Cells Can Both Remyelinate and Rescue the Otherwise Lethally Hypomyelinated Shiverer Mouse," *Cell Stem Cell* 2:553-565 (2008), which are hereby incorporated by reference in their entirety).

Example 6 hiPSC OPCs Efficiently Generate Astrocytes and OLs In Vivo

Besides the large numbers of hiPSC OPCs that differentiated as myelinogenic OLs in the shiverer mouse brain, large numbers also remained as resident OLIG2+ and NG2+ progenitor cells, and many OPCs of all three hiPSC lines differentiated as astrocytes as well, particularly as fibrous astrocytes of the white matter (FIGS. 6D, 6F, and 6I). When hiPSC-OPC-transplanted mice were assessed at 13 weeks after neonatal graft, most donor cells persisted as progenitors or had initiated oligodendroglial differentiation; by that time point, the net proportion of OLIG2+ cells, which included both OPCs and oligodendroglia, arising from all K04 and C27 transplanted cells was 78.7±2.4%, whereas the remainder were largely donor-derived GFAP+ astroglia (Table 5 below).

Interestingly, despite the widespread infiltration of the recipient brains by hiPSC OPCs, substantial astrocytic differentiation was noted by those cells within the presumptive white matter, within which the donor cells differentiated as morphologically apparent fibrous astrocytes, in close association with hiPSC derived OLs. These hiPSC-derived astrocytes might have been generated from lineage-restricted hiPSC-derived astrogliogenic precursors or by astrocytic differentiation in situ from still-bipotential hOPCs. In either case, by 3 months after neonatal transplant, the callosal and capsular white matter of shiverer recipients of OPC grafts derived from all three hiPSC lines manifested human astrocytic scaffolds harboring densely engrafted myelinogenic OLs, in each case yielding substantially reconstructed and densely myelinated central white matter (FIGS. 6D, 6F, and 6I).

TABLE 5

Phenotypic Differentiation of hiPSC-OPC
Derivatives In Vivo at 13 Weeks of Age

| Marker | C27-13 weeks (n = 4)<br>Mean ± SEM | K04-13 weeks (n = 5)<br>Mean ± SEM |
|---|---|---|
| OLIG2 | 68.0 ± 9.5% | 87.2 ± 9.9% |
| MBP | 12.0 ± 3.8% | 4.7 ± 1.1% |
| hGFAP | 11.6 ± 5.1% | 0.9 ± 0.5% |
| Ki67 | 8.5 ± 2.9% | 12.6 ± 3.2% |

Immunolabeling of engrafted mice at 13 weeks of age revealed that a majority of engrafted hiPSC OPCs and their progeny remained as OLIG2$_+$/hGFAP_ MBP_ OPCs; nonetheless, significant complements of hiPSC-derived MBP$_+$ oligodendroglia were noted in the engrafted mice, as were hGFAP$_+$ astrocytes, especially in OPCs derived from the C27 line. The Ki67 index at 13 weeks was relatively high, but no higher than that of neonatally-delivered fetal tissue-derived OPCs at the same postnatal age.

Example 7

Neonatal Engraftment with hiPSC OPCs could Rescue the Shiverer Mouse

Figures 8A, 8B, 8C, 8D, 8E:
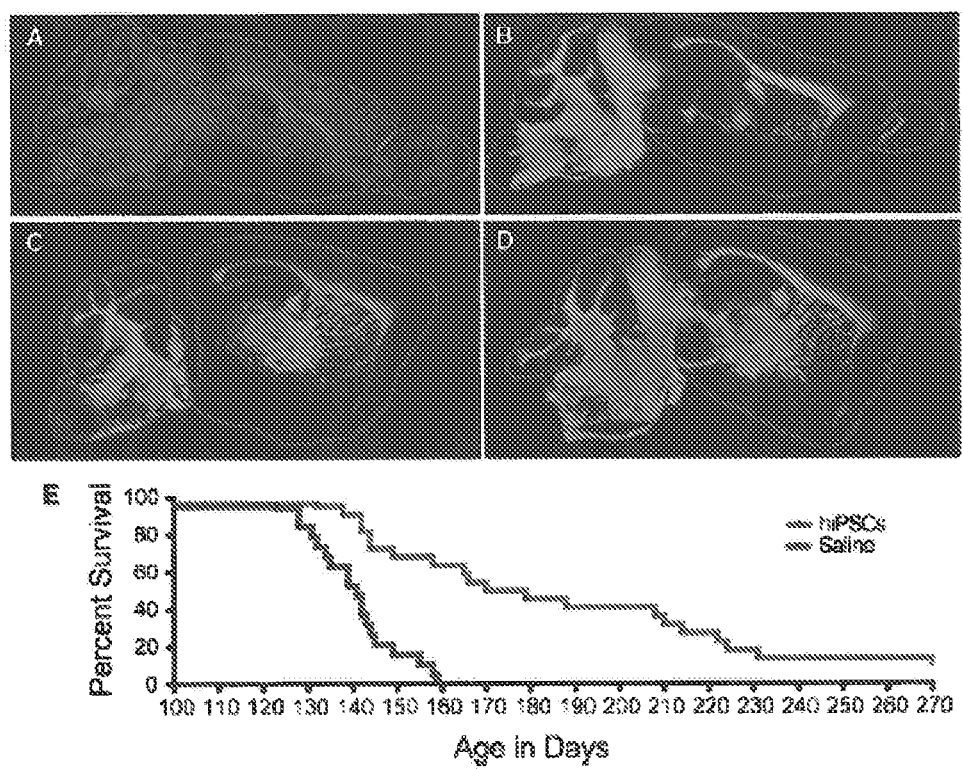
FIGS. 8A-8E show that hiPSC OPCs myelinate widely to greatly extend the survival of hypomyelinated mice.
Figure 9:
FIG. 9 shows widespread myelination by K04-Derived hiPSC OPCs Myelination by K04-derived hiPSC OPCs in coronal sections of neonatally-engrafted shiverer brain, at 4.5 months of age. MBP, green. Scale: 2 mm.

Whether the robust engraftment and myelination noted in transplanted shiverer mice were sufficient to ameliorate neurological deterioration and prolong the survival of shiverer mice, which typically die by 20 weeks of age, was assessed. To this end, a set of 22 neonatal homozygous shiverer×rag2 nulls were transplanted with 300,000 C27-derived hiPSC OPCs using a five-site forebrain and brain-stem injection protocol that achieves whole-neuraxis engraftment via transplanted OPCs (FIGS. 8A-8D) (Windrem et al., "Neonatal Chimerization With Human Glial Progenitor Cells Can Both Remyelinate and Rescue the Otherwise Lethally Hypomyelinated Shiverer Mouse," *Cell Stem Cell* 2:553-565 (2008), which is hereby incorporated by reference in its entirety). A matched set of 19 littermate controls were injected only with saline, and both sets were housed without further manipulation. Predictably, the 19 unimplanted shiverer controls died before 5 months of age, with a median survival of 141 days. In contrast, 19 of the 22 implanted mice lived longer than the longest-lived control mouse. The transplanted mice exhibited greatly prolonged survival (FIG. 8E), with reduced death over the 9 month period of observation, after which the experiment was terminated so that surviving mice could be processed for both immunohistochemical assessment of late-stage myelination and nodal reconstitution and for ultrastructural analysis (see Example 8). Comparison of the Kaplan-Meier survival plots of transplanted and control mice revealed a highly significant difference (chi square=17.95 by the Gehan-Breslow-Wilcoxon test; p<0.0001) (FIG. 8E). Those transplanted mice that survived beyond 6 months uniformly exhibited substantial myelination of the brain, brainstem, and cerebellum (FIGS. 8A-8D and 9). Remarkably, the time-point-matched degree of cerebral myelination, as well as the proportion of shiverers alive at any given time point, was greater in hiPSC-OPC-engrafted mice than in mice previously engrafted with fetal-human-tissue derived, A2B5-sorted OPCs (Windrem et al., "Neonatal Chimerization With Human Glial Progenitor Cells Can Both Remyelinate and Rescue the Otherwise Lethally Hypomyelinated Shiverer Mouse," *Cell Stem Cell* 2:553-565 (2008), which is hereby incorporated by reference in its entirety), which had otherwise been treated identically.

Example 8 hiPSC OPCs Generated Ultrastructurally Mature Myelin with Nodal Reconstitution

In light of the markedly extended survival of hiPSC-OPC-transplanted mice, whether this was associated with the formation of ultrastructurally compact myelin around host axons by hiPSC OLs was examined. To this end, electron microscopy was used on samples of corpus callosum derived from 22- to 36-week-old engrafted shiverers (n=3). These mice comprised animals that had been subjected to the five-site injection protocol and survived significantly longer than their unengrafted controls; these apparently rescued mice were killed after relatively long survival time points to permit assessment of their myelin integrity and quality. The recipient callosa were densely myelinated by mature compact myelin characterized by concentrically organized major dense lines (FIGS. 10A-10E) and interlaminar tight junctions (FIGS. 10F, 10G, and 11C); and the engrafted callosa were quite unlike those of their untransplanted shiverer controls, which failed to exhibit major dense lines or any other evidence of myelin compaction (FIGS. 11B, 11D, and 11E).

Figures 10A, 10B, 10C, 10D, 10E, 10F, 10G, 10H, 10I:
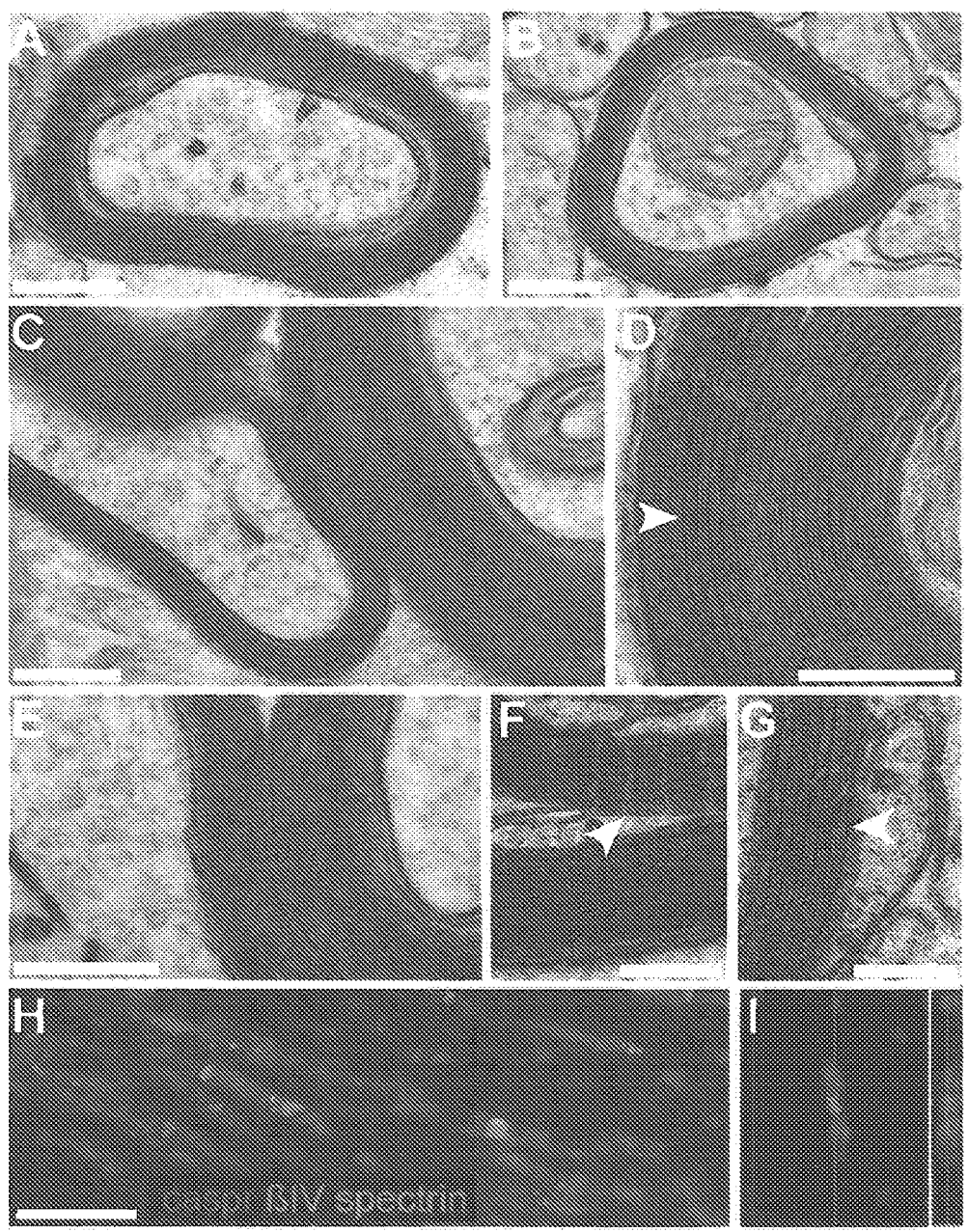
FIGS. 10A-10I show hiPSC-derived oligodendrocytes produce compact myelin and induce Nodes of Ranvier. Representative electron microscopic images of sections through the corpus callosum (FIGS. 10A and 10B) and ventral pons (FIG. 10C) of a 40-week-old shiverer mouse neonatally engrafted with C27 hiPSC OPCs, showing donor-derived compact myelin with evident major dense lines, ensheathing mouse axons.

Anatomic reconstitution of nodes of Ranvier was also noted in these mice, as determined by immunolabeling of Caspr and βIV spectrin, which respectively identified paranodal and nodal segments of newly myelinated axons (FIGS. 10H and 10I). In past studies, the anatomic and antigenic reconstitution of nodal architecture was correlated with the restoration of both rapid conduction and functional competence (Windrem et al., "Neonatal Chimerization With Human Glial Progenitor Cells Can Both Remyelinate and Rescue the Otherwise Lethally Hypomyelinated Shiverer Mouse," *Cell Stem Cell* 2:553-565 (2008), which is hereby incorporated by reference in its entirety). The rapid and robust reacquisition of nodal architecture in these mice indicates that hiPSC-derived OLs generate the cues necessary for the nodal organization of axonal proteins, upon which the formation of functional nodes of Ranvier depends.

Together, these data indicate that hiPSC-derived OPCs can efficiently generate OLs, which in turn can robustly myelinate the hypomyelinated shiverer forebrain, and that the myelin thereby generated is able to restore nodal architecture as well as to ensheath axons as efficiently as purified isolates of fetal-tissue-derived OPCs.

Example 9 hiPSC OPCs were Nontumorigenic In Vivo

Figures 4J, 4K, 4L, 4M:
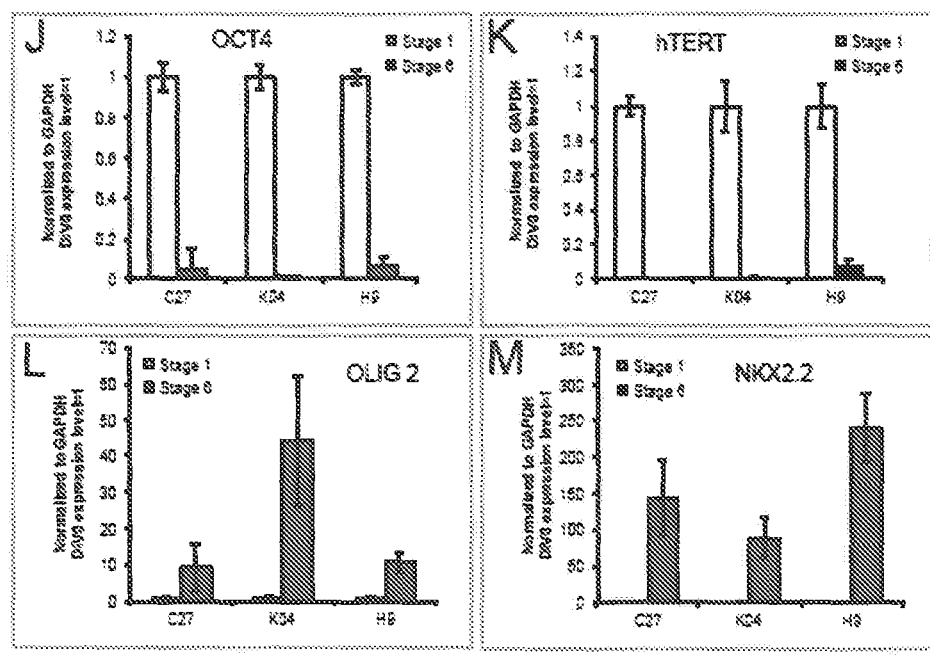

The persistence of undifferentiated pluripotent stem cells may cause either teratomas or neuroepithelial tumors in graft recipients (Roy et al., "Functional Engraftment of Human ES Cell-Derived Dopaminergic neurons Enriched by Coculture With Telomerase-Immortalized Midbrain Astrocytes," *Nat. Med.* 12:1259-1268 (2006), which is hereby incorporated by reference in its entirety). To assess whether any pluripotent or incompletely differentiated hESCs or hiPSCs remained in nominally fully differentiated OL cultures, both immunolabeling and qRT-PCR were used to assess the expression of pluripotent markers by late-stage hiPSC-derived OPCs. By 100 DIV, no detectable OCT4, NANOG, or SSEA4 protein could be found in OPCs derived from any of the hESC and hiPSC lines used in this study. Similarly, qRT-PCR revealed that transcripts of OCT4 and human telomerase reverse transcriptase (hTERT) were downregulated to essentially undetectable levels by 95 or more DIV (FIGS. 4J and 4K). The in vivo expression of OCT4, NANOG, and SSEA4 by engrafted OPCs 3 months after transplantation was examined. As noted, only a small minority of hNA+ donor cells were unstained by OLIG2, MBP, or GFAP. Many donor-derived cells expressed nestin or SOX2, indicating their persistence as neural progenitors, but no persistent expression of OCT4, NANOG, or SSEA4 was detectable in any of these cells, from any of the lines assessed.

Accordingly, no evidence of teratoma formation was found in any of the 16 shi/shi×rag2$^{-/-}$ mice examined for this purpose, which included mice transplanted neonatally with 100,000 cells and killed either 3 (n=11) or 4.5 (n=5) months later. Available mice in the survival series were also examined, all of whom had been transplanted at five sites with a total of 300,000 cells and had died between 4 and 9 months of age (n=10); none had any evidence of teratomas, heterotopias, or any type of tumor formation. In addition, hiPSCs were transplanted into normally myelinated rag2-null mice to assess tumorigenicity in the wild-type myelin environment as well. Of five mice examined 6 months after transplantation, none showed any evidence of tumor formation, heterotopias, or even foci of undifferentiated expansion. Of note, persistent expression of SOX2, KLF4, and c-MYC mRNA was noted by qPCR in the hiPSC-derived cells, reflecting some level of unsilenced expression of the lentivirally inserted reprogramming genes; nonetheless, the expression of the these transcripts was not associated with tumorigenesis by cells transplanted at the end of stage 6.

The lack of tumor formation in hiPSC-OPC-engrafted mice was associated with a significant decrease in the mitotic fraction of the implanted hiPSC OPCs as a function of time after graft. hiPSC OPC proliferation in vivo was measured as Ki67 expression by all human donor cells, which was noted to decrease linearly from 3 months (13.6±0.6%) to 6 months (4.3±0.04%) of age (R2=0.9; p=0.001; n=7).

To establish the role of the differentiation protocol in diminishing the risk of tumorigenesis, rag2-null mice were also transplanted with both C27 and K04 hiPSCs at the end of stages 1 and 3. This was also done as a positive control for tumor detection, given the lack of observed tumors in the hiPSC OPC (stage 6)-engrafted mice, as much as 9 months after transplant. Yet in contrast to the hiPSC-OPC-engrafted mice, which were entirely tumor-free, every animal engrafted with earlier-stage hiPSCs manifested histologically overt tumor formation by 3 months (n=8 mice engrafted with stage 1 hiPSCs; n=6 with stage 3 cells). Thus, the differentiation protocol appeared to effectively deplete the donor cell pool of persistent undifferentiated cells; the resultant grafts of hiPSC OPCs proved uniformly nontumorigenic when studied as long as 9 months after transplant.

Discussion of Examples 1-9

In this study, the feasibility of using hiPSCs to generate highly enriched populations of both astrocytes and myelinogenic central OLs, with high efficiency and yield has been established. The success of the protocol described herein in all four lines used in this study, which include WA09/H9 hESCs and K04, C14, and C27 iPSCs, indicates its broad applicability, and the highly efficient gliogenesis afforded by this strategy indicates its robust nature. Most importantly, the robust myelination that was noted in vivo, which compared favorably to that previously demonstrated by tissue derived fetal human glial progenitors, indicated the probable functional integration and utility of these grafts. Accordingly, it was noted that myelination-deficient shiverers engrafted neonatally with hiPSC OPCs survived substantially longer than did both their untransplanted and saline-injected controls; indeed, over three-fourths of hiPSC-OPC-transplanted mice survived over 6 months, long after all untreated control mice had died. As a result, hiPSC OPCs from single-patient skin samples can now be reliably produced in sufficient numbers to provide myelinogenic autografts largely, though perhaps not completely (Zhao et al., "Immunogenicity of Induced Pluripotent Stem Cells," *Nature* 474:212-215 (2011), which is hereby incorporated by reference in its entirety), free of rejection risk.

Importantly, the myelination efficiency of the implanted iPSC derived OPCs, defined as the proportion of central axons myelinated as a function of time after graft, proved as high as that which was had previously achieved using tissue-derived, CD140a sorted OPCs (Sim et al., "CD140a Identifies a Population of Highly Myelinogenic, Migration-Competent and Efficiently Engrafting Human Oligodendrocyte Progenitor Cells," *Nat. Biotechnol.* 29:934-941 (2011), which is hereby incorporated by reference in its entirety). Indeed, it was remarkable to note that the proportion of axons ensheathed was as high in enriched but unsorted hiPSC-OPC grafts as in fetal-tissue-derived OPC grafts that had been sorted for CD140a+ cells prior to transplant. Indeed, the hiPSC-OPCs grafts myelinated more axons more rapidly than did A2B5+/PSA-NCAM-sorted fetal-tissue derived cells, probably reflecting the higher proportion of bipotential glial progenitor cells in the hiPSC-OPC populations by the time of their harvest and transplantation.

In light of the robust myelination afforded by hiPSC-OPC grafts, it was asked whether neonatal transplantation of hiPSC OPCs might be sufficient to rescue the phenotype and survival of recipient shiverer homozygotes, as had previously been observed in a minority of shiverers transplanted with fetal-human brain-derived OPCs. The hiPSC-OPC-transplanted mice indeed exhibited markedly improved survival; death was both delayed and reduced overall in the transplanted group over the 9 month period of observation. As previously documented with fetal-brain-tissue-derived OPC grafts, the rescued mice manifested progressive resolution of their neurological deficits (Windrem et al., "Neonatal Chimerization With Human Glial Progenitor Cells Can Both Remyelinate and Rescue the Otherwise Lethally Hypomyelinated Shiverer Mouse," *Cell Stem Cell* 2:553-565 (2008), which is hereby incorporated by reference in its entirety). Remarkably, however, the proportion of animals whose survival benefitted from hiPSC-OPC transplantation was substantially higher than that which was previously reported using tissue-derived human OPCs: whereas it was observed that only one-quarter of shiverer mice transplanted with tissue-derived OPCs survived beyond 6 months of age (Windrem et al., "Neonatal Chimerization With Human Glial Progenitor Cells Can Both Remyelinate and Rescue the Otherwise Lethally Hypomyelinated Shiverer Mouse," *Cell Stem Cell* 2:553-565 (2008), which is hereby incorporated by reference in its entirety), in the present study over half of the hiPSC-OPC-engrafted mice did so (FIG. 8E). Nonetheless, some later deaths beyond 7 months of age were still noted; this may reflect an inhomogeneous dispersal of hiPSC OPCs that was observed in some animals, the nature of which is under investigation. Those late deaths notwithstanding, at least one-fifth of the mice appeared to represent outright clinical rescues, though these survivors were sacrificed at ≥9 months for histological and ultrastructural analysis. These provocative data demonstrate the superiority of hiPSC OPCs as therapeutic vectors, perhaps by virtue of their more rapid myelinogenesis, which may be a function of the prolonged differentiation conditions that was employed in this OPC induction protocol.

Interestingly, no evidence of tumorigenesis from implanted hiPSC-derived glial progenitors was observed at time points as long as 9 months after transplant. This was surprising, given that previous studies had provided ample evidence for the risk of tumor formation from either residual undifferentiated cells (Pruszak et al., "CD15, CD24, and CD29 Define a Surface Biomarker Code for Neural Lineage Differentiation of Stem Cells," Stem Cells 27:2928-2940 (2009), which is hereby incorporated by reference in its entirety) or from partially differentiated neuroepithelial cells in hESC-derived transplants (Roy et al., "Functional Engraftment of Human ES Cell-Derived Dopaminergic neurons Enriched by Coculture With Telomerase-Immortalized Midbrain Astrocytes," Nat. Med. 12:1259-1268 (2006), which is hereby incorporated by reference in its entirety). It is possible that the prolonged differentiation protocols employed to produce OPCs are robust enough to effectively eliminate any residual undifferentiated cells prior to transplantation. It is similarly possible that epigenetic marks persisting in reprogrammed hiPSCs effectively lowered the later risk of tumorigenesis by their differentiated derivatives. In any case, even longer survival time points will be needed, with more animals and an intensive search for any residual undifferentiated and/or potentially tumorigenic cells in vivo, before one can confidently state the safety of these grafts. Should tumorigenesis at any point be a concern, then hiPSC OPCs may be sorted to purity before transplantation, on the basis of the high incidence of definitively pro-oligodendrocytic $CD9^+/CD140a^+$ cells in the cultures, and the ability to isolate these cells by fluorescence-activated cell sorting (FACS) based upon these coexpressed epitopes (Sim et al., "CD140a Identifies a Population of Highly Myelinogenic, Migration-Competent and Efficiently Engrafting Human Oligodendrocyte Progenitor Cells," Nat. Biotechnol. 29:934-941 (2011), which is hereby incorporated by reference in its entirety).

These findings indicate that high-efficiency in vivo oligodendrocytic differentiation and myelination can be achieved from hiPSCs, indicating the utility of iPSC-derived autografts in treating acquired disorders of myelin. Yet it is also important to note the efficient, context-dependent generation of both fibrous and protoplasmic astrocytes from engrafted hiPSC OPCs. Besides the importance of astroglia in effecting the structural and physiological reconstitution of dysmyelinated tracts, astrocytic engraftment may be of particular importance in correcting dysmyelinating disorders of enzyme deficiency, given that astrocytic lysosomal enzymes have been found to readily transit from wild-type to deficient glia within brain tissue, in a manner potentially sufficient to rescue enzyme-deficient hosts (Lee et al., "Stem Cells Act Through Multiple Mechanisms to Benefit Mice With Neurodegenerative Metabolic Disease," Nat. Med. 13:439-447 (2007), which is hereby incorporated by reference in its entirety). In addition, hiPSC-derived astrocytes may prove to be critically important therapeutic vectors for diseases of primarily astrocytic pathology (Krencik et al., "Specification of Transplantable Astroglial Subtypes From Human Pluripotent Stem Cells," Nat. Biotechnol. 29:528-534 (2011), which is hereby incorporated by reference in its entirety), such as Alexander disease and the vanishing white-matter disorders (Bugiani et al., "Defective Glial Maturation in Vanishing White Matter Disease," J. Neuropathol. Exp. Neurol. 70:69-82 (2011), which is hereby incorporated by reference in its entirety), in which myelin loss occurs but may be secondary to astrocytic dysfunction. In each of these cases, however, the therapeutic use of iPSC-derived astroglia will need to be paired with methods for the ex vivo correction of the genetic defects characteristic of these disorders.

Human iPSC OPCs might thus be attractive vectors for restoring or replacing glial populations in a variety of disease settings. Most critically, the data presented herein indicates the preferential use of hiPSC-derived OPCs to restore lost myelin in disorders such as multiple sclerosis and traumatic demyelination, in which no genetic abnormalities might complicate the use of a patient's own somatic cells as the iPSC source. iPSC OPCs may similarly prove of great therapeutic value in genetic disorders of myelin, such as Pelizaeus-Merzbacher disease, recognizing that the underlying genetic defect must first be repaired in the donor somatic cells before glial progenitor induction and implantation. The present study thus establishes the technical feasibility and efficacy of generating myelinogenic OLs from hiPSCs and indicates the clinical situations in which this approach might be most appropriate. The clinical application of patient-specific, somatic cell-derived glial progenitor cell transplants for the treatment of acquired disorders of myelin, as well as of the broader spectrum of human glial pathologies can now be reasonably contemplated.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A population of cells derived from human induced pluripotent stem cells, wherein greater than 30% of said population comprises human oligodendrocyte progenitor cells, wherein said human oligodendrocyte progenitor cells in the population co-express oligodendrocyte transcription factor 2 (OLIG2) and CD140a/platelet derived growth factor receptor-α (PDGFRα), and wherein less than 12% of the cells of the population are oligodendrocytes expressing the surface lipid sulfatide recognized by the O4 antibody.

2. The population of claim 1, wherein the oligodendrocyte progenitor cells of the population further express SRY Box 10 (SOX10), CD9, or a combination thereof.

3. The population of claim 1, wherein said population of cells does not contain microtubule-associated protein 2 (MAP2) expressing neurons.

4. The population of claim 1, wherein said population contains less than 1% residual pluripotent cells.

5. The population of claim 1, wherein said population has an in vivo myelination efficiency that is greater than the in vivo myelination efficiency of a population of A2B5$^+$/polysialylated-neural cell adhesion molecule (PSA-NCAM$^-$)sorted fetal human tissue derived oligodendrocyte progenitor cells.

6. The population of claim 1, wherein said population is capable of achieving an in vivo myelination density upon engraftment which is greater than that achieveable with a population of A2B5$^+$/PSA-NCAM$^-$ sorted fetal human tissue derived oligodendrocyte progenitor cells.

7. The population of claim 1, wherein said population is capable upon engraftment of achieving improved survival in a myelination deficient mammal compared to that achieveable with a population of A2B5$^+$/PSA-NCAM$^-$ sorted fetal human tissue derived oligodendrocyte progenitor cells.

8. The population of claim 1, wherein 4%-12% of the cells of the population are oligodendrocytes expressing the surface lipid sulfatide recognized by the O4 antibody.

9. The population of claim 1, wherein greater than 50% of said population comprises human oligodendrocyte progenitor cells.

* * * * *